US007932243B2

(12) United States Patent
Yoo

(10) Patent No.: US 7,932,243 B2
(45) Date of Patent: *Apr. 26, 2011

(54) BILE PREPARATIONS FOR GASTROINTESTINAL DISORDERS

(76) Inventor: Seo Hong Yoo, Wyckoff, NJ (US)

(*) Notice: Subject to any disclaimer, the term of this patent is extended or adjusted under 35 U.S.C. 154(b) by 287 days.

This patent is subject to a terminal disclaimer.

(21) Appl. No.: 11/373,554

(22) Filed: Mar. 10, 2006

(65) Prior Publication Data

US 2006/0188530 A1 Aug. 24, 2006

Related U.S. Application Data

(63) Continuation-in-part of application No. 11/251,137, filed on Oct. 14, 2005, now Pat. No. 7,772,220, and a continuation-in-part of application No. 09/778,154, filed on Feb. 5, 2001, now Pat. No. 7,303,768, and a continuation-in-part of application No. 09/357,549, filed on Jul. 20, 1999, now Pat. No. 6,251,428.

(60) Provisional application No. 60/619,199, filed on Oct. 15, 2004, provisional application No. 60/180,268, filed on Feb. 4, 2000, provisional application No. 60/094,069, filed on Jul. 24, 1998.

(51) Int. Cl.
*A61K 31/575* (2006.01)
*C07J 9/00* (2006.01)

(52) U.S. Cl. ......... 514/182; 552/549; 552/551; 552/552

(58) Field of Classification Search .................. None
See application file for complete search history.

(56) References Cited

U.S. PATENT DOCUMENTS

| | | | | |
|---|---|---|---|---|
| 3,845,770 | A | 11/1974 | Theeeuwes et al. | 128/260 |
| 3,916,899 | A | 11/1975 | Theeeuwes et al. | 128/260 |
| 4,036,954 | A | 7/1977 | Murakami et al. | 424/176 |
| 4,092,428 | A | 5/1978 | Murakami et al. | 424/317 |
| 4,113,882 | A | 9/1978 | Okazaki et al. | 424/317 |
| 4,320,146 | A | 3/1982 | Walser | 424/319 |
| 4,327,725 | A | 5/1982 | Cortese et al. | 128/260 |
| 4,585,790 | A | 4/1986 | Padfield et al. | 514/471 |
| 4,681,876 | A | 7/1987 | Marples et al. | 514/182 |
| 4,879,303 | A | 11/1989 | Davison et al. | 514/356 |
| 5,057,321 | A | 10/1991 | Edgren et al. | 424/413 |
| 5,149,537 | A | 9/1992 | Azria et al. | 424/436 |
| 5,157,022 | A | 10/1992 | Barbul | 514/18 |
| 5,260,074 | A | 11/1993 | Sipos | 424/497 |
| 5,292,534 | A | 3/1994 | Valentine et al. | 424/451 |
| 5,300,300 | A | 4/1994 | Egidio et al. | 424/456 |
| 5,302,398 | A | 4/1994 | Egidio et al. | 424/474 |
| 5,302,400 | A | 4/1994 | Sipos | 424/494 |
| 5,310,560 | A | 5/1994 | Widauer | 424/451 |
| 5,324,514 | A | 6/1994 | Sipos | 424/94.63 |
| 5,342,625 | A | 8/1994 | Hauer et al. | 424/455 |
| 5,380,533 | A | 1/1995 | Egidio et al. | 424/456 |
| 5,446,026 | A | 8/1995 | Ruff et al. | 514/15 |
| 5,470,581 | A | 11/1995 | Grillo et al. | 424/479 |
| 5,484,776 | A | 1/1996 | Racz et al. | 514/54 |
| 5,516,523 | A | 5/1996 | Heiber et al. | 424/435 |
| 5,534,505 | A | 7/1996 | Widauer | 514/169 |
| 5,578,304 | A | 11/1996 | Sipos | 424/94.1 |
| 5,599,926 | A | 2/1997 | Still et al. | 540/456 |
| 5,641,767 | A | 6/1997 | Wess et al. | 514/172 |
| 5,653,987 | A | 8/1997 | Modi et al. | 424/400 |
| 5,686,588 | A | 11/1997 | Yoo | 536/13.3 |
| 5,750,104 | A | 5/1998 | Sipos | 424/94.21 |
| 5,750,707 | A | 5/1998 | Spargo | 546/321 |
| 5,843,929 | A | 12/1998 | Larson et al. | 514/182 |
| 5,846,964 | A | 12/1998 | Ozeki | 514/182 |
| 5,858,998 | A | 1/1999 | Leuschner | 514/171 |
| 5,863,550 | A | 1/1999 | Maeda et al. | 424/423 |
| 5,898,028 | A | 4/1999 | Jensen et al. | 514/4 |
| 5,945,411 | A | 8/1999 | Larson et al. | 514/171 |
| 5,965,164 | A | 10/1999 | Fuisz et al. | 424/489 |
| 5,977,070 | A | 11/1999 | Piazza et al. | 514/12 |
| 6,099,859 | A | 8/2000 | Cheng et al. | 424/464 |
| 6,210,699 | B1 | 4/2001 | Acharya et al. | 424/435 |
| 6,245,753 | B1 | 6/2001 | Byun et al. | 514/56 |
| 6,251,428 | B1 * | 6/2001 | Yoo | 424/455 |
| 6,309,663 | B1 * | 10/2001 | Patel et al. | 424/450 |

(Continued)

FOREIGN PATENT DOCUMENTS

AU 37358/99 12/1999

(Continued)

OTHER PUBLICATIONS

Remington: The science and Practice of Pharmacy, published 2000 by Lippincott Williams and Wilkins, p. 218.*
2006 Chemical Abstracts catalog, published 2006 by Chemical Abstracts Service, p. 52.*
Merriam-Webster's Collegiate Dictionary, Tenth Edition, published 1998 by Merriam-Webster, Incorporated, p. 924.*
Notification Concerning Transmittal of International Preliminary Report on Patentability; PCT/US2006/008925; pp. 6, Apr. 16, 2008.
"Dacarbazine", Aidsmap Treatment and Care, http://www.aidsmap.com/en/docs/9685F4D7-D57C-4F10-A41F-D5EDF7811B3A.asp, pp. 1, Feb. 6, 2006.

(Continued)

*Primary Examiner* — Eric S Olson
(74) *Attorney, Agent, or Firm* — Baker Botts L.L.P.

(57) ABSTRACT

The present disclosure relates to methods and compositions to offset, ameliorate and/or alleviate one or more unwanted and/or adverse gastrointestinal effects. For example, in some embodiments, the present disclosure relates to compositions that include a bile acid, a carbohydrate and/or a pharmaceutical compound, wherein the pharmaceutical is associated with an adverse gastrointestinal effect in a subject (e.g., mammal or human). Non-limiting examples of pharmaceutical compounds may include a nonsteroidal anti-inflammatory drug, a gastric irritating drug (e.g., an antibiotic, an adrenal cortocoid steroid and an anti-cancer drug) and combinations thereof. The disclosure further relates to methods of ameliorating or eliminating at least one adverse gastrointestinal effects of a composition, comprising administering to a subject an aqueous solution comprising a bile acid and a carbohydrate.

29 Claims, 3 Drawing Sheets
(1 of 3 Drawing Sheet(s) Filed in Color)

U.S. PATENT DOCUMENTS

| | | | |
|---|---|---|---|
| 6,383,471 B1* | 5/2002 | Chen et al. | 424/45 |
| 6,635,628 B2 | 10/2003 | Bouscarel et al. | 514/171 |
| 7,034,006 B2 | 4/2006 | Yedgar et al. | 514/42 |
| 7,166,299 B2* | 1/2007 | Yoo | 424/455 |
| 7,303,768 B2* | 12/2007 | Yoo | 424/528 |
| 2001/0046521 A1 | 11/2001 | Zasloff et al. | 424/649 |
| 2002/0031558 A1 | 3/2002 | Yoo | 424/653 |
| 2002/0081361 A1 | 6/2002 | Towb et al. | 426/548 |
| 2003/0044413 A1 | 3/2003 | Steer et al. | 424/145.1 |
| 2003/0186933 A1* | 10/2003 | Yoo | 514/54 |
| 2005/0158408 A1 | 7/2005 | Yoo | 424/728 |
| 2006/0051319 A1* | 3/2006 | Yoo | 424/85.1 |
| 2006/0089331 A1* | 4/2006 | Yoo | 514/58 |
| 2006/0142241 A1* | 6/2006 | Yoo | 514/59 |
| 2006/0188530 A1 | 8/2006 | Yoo | 424/400 |
| 2007/0072828 A1* | 3/2007 | Yoo | 514/60 |

FOREIGN PATENT DOCUMENTS

| | | |
|---|---|---|
| CN | 1450914 | 10/2003 |
| EP | 0086705 | 2/1983 |
| EP | 0312052 | 10/1988 |
| EP | 0 599 282 A1 | 6/1994 |
| EP | 1255566 A2 | 11/2002 |
| FR | 2710267 | 3/1995 |
| JP | 55 022616 A | 2/1980 |
| JP | 61171421 | 2/1986 |
| JP | 62153220 | 7/1987 |
| JP | 63104925 | 5/1988 |
| JP | 63243031 | 10/1988 |
| JP | 6024991 | 2/1994 |
| WO | WO 99/61481 | 12/1999 |
| WO | 0004875 | 2/2000 |
| WO | WO 01/56547 A2 | 8/2001 |
| WO | WO 2004/012686 | 2/2004 |
| WO | WO 2004/043342 A2 | 5/2004 |
| WO | 2004/096123 | 11/2004 |
| WO | WO 2006/026555 A2 | 3/2006 |
| WO | 2006/050165 | 5/2006 |
| WO | WO 2006/057637 A1 | 6/2006 |

OTHER PUBLICATIONS

"Drug Information: Dacarbazine", Medline Plus, http://www.nlm.nih.gov/medlineplus/druginfo/medmaster/a682750.html , pp. 2, Apr. 1, 2003.

"Dacarbazine", NCI Terminology Browser, http://nciterms.nci.nih.gov/NCIBrowser/PrintableReport.jsp?dictionary=NCI_Thesaurus&code=C411 , pp. 3, Nov. 2005.

P.J. Neveu, "The Effects of Thiol Moiety of Levamisole on Both Cellular and Humoral Immunity During the Early Response to a Hapten-Carrier Complex" Clin. Exp. Immunol. vol. 32, pp. 419-422, 1978.

E. Nagy et al., "Imuthiol Inhibits the Etoposide-Induced Apoptosis in HL-60 Cells" Immunology Letters vol. 64, pp. 1-4, 1998.

"An Assessment of the In Vivo Biological Effects of Diethyldithiocarbamate (DTC) in HIV-Infected Patients", ClinicalTrials.gov, http://www.clinicaltrials.gov/ct/show/NCT00000650;jsessionid=AF8903A542A345FA86641E2A559AC8C9?order=1 pp. 6, Feb. 27, 2006.

Hubner et al., "Enhancement of Monocyte Antimycobacterial Activity by Diethyldithiocarbamate (DTC)" Int. J. Immunopharmac. vol. 13, pp. 1067-1072, 1991.

"Diethyldithiocarbamate", http://nciterms.nci.nih.gov/NCIBrowser/ConceptReports.jsp? , pp. 2, Feb. 6, 2006.

"Proventil", PDR Health, http://www.pdrhealth.com/drug_info/rxdrugprofiles/drugs/pro1360.shtml, pp. 5, Feb. 8, 2006.

"Powered by Dorland's Illustrated Medical Dictionary: E", MerckSource, http://www.mercksource.com/pp/us/cns/cns_hl_dorlands.jspzQzpgzEzzSzp-pdocszSzuszSzcommonzSzdorlandszSzdorlandzSzdmd_e_17zPzhtm, pp. 3, Feb. 27, 2006.

F.S. Giorgi et al., "The role of norepinephrine in epilepsy: from the bench to the bedside" Neurosci. Behavioral. Rev.. vol. 28, pp. 507-524, 2004.

K. Bodin et al., "Antiepileptic drugs increase plasma levels of 4beta-hydroxycholesterol in humans: evidence for involvement of cytochrome p450 3A4" J. Biol. Chem. vol. 276, pp. 38685-38689, Oct. 19, 2001.

V.S. Kasture et al.,"Anticonvulsant activity of *Albizzia lebbeck* leaves" Indian Journal of Experimental Biology vol. 34, pp. 78-80, Jan. 1996.

V. Fontes et al., "Recurrent Aphthous Stomatitis: Treatment With Colchicine. An Open Trial of 54 Cases", Ann. Dermatol. Venereol. vol. 129, pp. 1365-1369 , (with abstract), 2002.

P.P. But et al., "Ethnopharmacology of bear gall bladder: I" Journal of Ethnopharmacology vol. 47, pp. 27-31, 1995.

K.G. Rajesh et al., "Hydrophilic Bile Salt Ursodeoxycholic Acid Protects Myocardium Against Reperfusion Injury in a P13K/Akt Dependent Pathway", Journal of Molecular and Cellular Cardiology, vol. 39, pp. 766-776, 2005.

Cecilia M.P. Rodrigues et al., "Ursodeoxycholic Acid May Inhibit Deoxycholic Acid-Induced Apoptosis by Modulating Mitochondrial Transmembrane Potential and Reactive Oxygen Species Production", Molecular Medicine, vol. 4, pp. 165-178, 1998.

"Drug Information: Hydralazine", Medline Plus, http://www.nlm.nih.gov/medlineplus/druginfo/medmaster/a682246.html , pp. 3, Apr. 1, 2003.

"Drug Information: Isoxsuprine (Systemic)", Medline Plus, http://www.nlm.nih.gov/medlineplus/druginfo/uspdi/202310.html , pp. 4, Jul. 15, 1994.

"Drug Information: Nylidrin (Systemic)", Medline Plus, http://www.nlm.nih.gov/medlineplus/druginfo/uspdi/202416.html , pp. 3, May 14, 1993.

"Drug Information: Dyphylline (Systemic)", Medline Plus, http://www.nlm.nih.gov/medlineplus/druginfo/uspdi/202752.html , pp. 4, Jun. 14, 1999.

"Drug Information: Bronchodilators, Andrenergic (Inhalation)", Medline Plus, http://www.nlm.nih.gov/medlineplus/druginfo/uspdi/202095.html , pp. 12, Jun. 25, 2003.

"Colfosceril Palmitate", Tiscali, http://www.tiscali.co.uk/lifestyle/healthfitness/health_advice/netdoctor/archive/100003422.html , pp. 2, 1998-2004.

"Selenium", PDR Health, http://www.pdrhealth.com/drug_info/nmdrugprofiles/nutsupdrugs/sel_0232.shtml, pp. 8, Feb. 27, 2006.

"Clean, Beautiful, Healthy Life ", LG Household & Health Care, http://www.lgcare.com/english/aboutus/06.html, pp. 3, Feb. 27, 2006.

"Zovirax", PDRhealth, http://www.pdrhealth.com/drug_info/rxdrugprofiles/drugs/zov1505.shtml , pp. 4, Feb. 8, 2006.

"Denavir", PDRhealth, http://www.pdrhealth.com/drug_info/rxdrugprofiles/drugs/den1123.shtml , pp. 2, Feb. 8, 2006.

V.S. Kasture et al.,"Anticonvulsive activity of *Albizzia lebbeck, Hibiscus rosa* sinesis and *Butea monosperma* in experimental animals" Journal of Ethnopharmacology vol. 71, pp. 65-75, 2000.

"Drug Information: Celecoxib", Medline Plus, http://www.nlm.nih.gov/medlineplus/druginfo/medmaster/a699022.html , pp. 4, Jan. 1, 2006.

R.L. Wynn, "New Reports on Dental Analgesics. NSAIDs and Cardiovascular Effects, Celecoxib for Dental Pain, and a New Analgesic—Tramadol With Acetaminophen" General Dentistry vol. 50, pp. 218-220, 222, May 2002.

R.L. Wynn, "Update on Nonprescription Pain Relievers for Dental Pain", General Dentistry vol. 52, pp. 94-98, Mar. 2004.

P.M. Preshaw et al., "Self-medication for the control of dental pain: what are our patients taking?", Dent Update vol. 21, pp. 299-301, 304, Sep. 1994.

A.D. McNaught, "Nomenclature of Carbohydrates", Pure and Applied Chemistry, vol. 68, pp. 1919-2008, 1996.

D.L. Nelson, "Carbohydrates and Glycobiology", Lehninger Principles of Biochemistry,Fourth Edition, pp. 238-271, 2005.

H.R. Horton, "Carbohydrates", Principles of Biochemistry, Second edition, pp. 228-234, 1996.

Gerhard Schmid, "Preperation and Industrial Production of Cyclodextrins", Comprehensive Supramolecular Chemistry, vol. 3, pp. 41-56, 1996.

Frömming, "Cyclodextrins", Cyclodextrins in Pharmacy, Chapter 1, pp. 1-18, 1994.

Frömming, "Cyclodextrin Derivatives", Cyclodextrins in Pharmacy, Chapter 2, pp. 19-32, 1994.

Lehninger et al., "Carbohydrates and Glycobiology", Principles of Biochemistry, pp. 301-307, 2000.

D.S. Alberts et al., "Phase III Trial of Ursodeoxycholic Acid to Prevent Colorectal Adenoma Recurrence", Journal of National Cancer Institute, vol. 97, No. 11, pp. 846-853, Jun. 1, 2005.

D. Gaist et al.; "Statins and Risk of Polyneuropathy"; Neurology, vol. 58; pp. 1333-1337, May 2002.

D. Chapman-Shimshoni et al.; "Simvastatin Induces Apoptosis of B-CLL cells by Activation of Mitochondrial Caspase 9"; Experimental Hematology, vol. 31; pp. 779-783, 2003.

C.J. Newton et al.; "Fluvastin Induces Apoptosis of Vascular Endothelial Cells: Blockade by Glucocorticoids"; Cardiovascular Surgery, vol. 11, No. 1; pp. 52-60, 2003.

M.A. Vandelli et al.; "2-Hydroxypropyl-β-Cyclodextrin Complexation With Ursodeoxycholic Acid"; International Journal of Pharmaceutics, vol. 118; pp. 77-83, 1995.

J.F. Dasta et al.; "Comparison of Visual and Turbidimetric Methods for Determining Short-Term Compatibility of Intravenous Critical-Care Drugs"; American Journal of Hospital Pharmacy; vol. 45; pp. 2361-2366, Nov. 1988.

C.A. Ventura et al.; "Improvement of Water Solubility and Dissolution Rate of Ursodeoxycholic Acid and Chenodeoxycholic Acid by Complexation With Natural and Modified β-Cyclodextrins"; International Journal of Pharmaceutics; vol. 149; pp. 1-13, 1997.

M. Föcking et al; "Statins Potentiate Caspase-3 Activity in Immortalized Murine Neurons"; Neuroscience Letters; vol. 355; pp. 41-44, 2003.

Michael B. Jacobs; "HMG-CoA Reductase Inhibitor Therapy and Peripheral Neuropathy"; www.PubMed.com ; pp. 3, Jun. 1, 1994.

Chad Silverberg; "Atorvastatin-Induced Polyneuropathy"; www.PubMed.com ; pp. 5, Nov. 4, 2003.

A.C. Peltier et al.; "Recent Advances in Drug-Induced Neuropathies"; Current Opinion in Neurology, vol. 15; pp. 633-638, 2002.

Park et al.; "Cisplatin-Induced Apoptotic Cell Death in Mouse Hybrid Neurons Is Blocked by Antioxidants Through Suppression of Cisplatin-Mediated Accumulation of p53 but Not of Fas/Fas Ligand"; Journal of Neurochemistry, vol. 75, No. 3; pp. 946-953, 2000.

R. Panini et al.; "Improvement of Ursodeoxycholic Acid Bioavailability by 2-Hydroxypropyl-β-Cyclodextrin Complexation in Healthy Volunteers"; Pharmacological Research; vol. 31, No. 314; pp. 205-209, 1995.

Invernizzi et al.; "Difference in the Metabolism and Disposition of Ursodeoxycholic Acid and of its Taurine-Conjugated Species in Patients with Primary Biliary Cirrhosis"; Hepatology, vol. 29, No. 2; pp. 320-327, 1999.

Itoh et al.; "Antibacterial action of bile acids against *Helicobacteria pylori* and changes inits ultrastructural morphology: effect of unconjugated dihydroxy bile acid"; J. Gastroenterol, vol. 34, pp. 571-576, 1999.

Knopp et al., "Long-Term Blood Cholesterol-Lowering Effects of a Dietary Fiber Supplement", Am J Pre. Med (1999) 17(1):18-23, 1999.

F. Lanzarotto et al., "Effect of Long-Term Simvastatin Administration as an Adjunct to Ursodeoxycholic Acid: Evidence for a Synergistic Effect on Biliary Bile Acid Composition but Not on Serum Lipids in Humans", GUT, (1999) vol. 4 pp. 552-556, 1999.

Leuschner et al., "Oral Budesonide and Ursodeoxycholic Acid for Treatment of Primary Biliary Cirrhosis: Results of a Prospective Double-Blind Trial", Gastroenterology, (1999) vol. 117 pp. 918-925, 1999.

Na et al., "Cloud Point of Nonionic Surfactants: Modulation with Pharmaceutical Excipients", Pharmaceutical Research, (1999) vol. 16, No. 4 pp. 562-568, 1999.

Osato et al., "Osmotic Effect of Honey on Growth and Viability of *Helicobacter pylori*", Digestive Diseases and Sciences, (1999) vol. 44, No. 3 pp. 462-464, 1999.

Sinisalo et al., "Ursodeoxycholic Acid and Endothelial-Dependent, Nitric Oxide-Independent Vasodilatation of Forearm Resistance Arteries in Patients with Coronary Heart Disease", Br. J. Clin. Pharamcol., (1999) vol. 47 pp. 661-665, 1999.

Verrips et al., "Effect of Simvastatin in Addition to Chenodeoxycholic Acid in Patients with Cerebrotendinous Xanthomatosis", Metabolism, (1999) vol. 48, No. 2 pp. 233-238, 1999.

Wacker Biochem. Corp., advertisement, *C&EN*, 31 (Apr. 12, 1999).

M. A. Hammad, B. W. Müller, Increasing Drug Solubility by Means of Bile Salt-Phosphatidylcholine-Based Mixed Micelles, European J. of Pharmaceutics and Biopharmaceutics. (1998) vol. 46 pp. 361-367.

M. A. Hammad et al., "Solubility and Stability of Tetrazepam in Mixed Micelles", European J. of Pharmaceutical Sciences, (1998) vol. 7 pp. 49-55.

Oliva et al., "Ursodeoxycholate Alleviates Alcoholic Fatty Liver Damage in Rats", Alcohol Clin Exp Res., (1998), vol. 22, No. 7,pp. 1538-1543.

Rodrigues et a;l, "Ursodeoxycholic Acid May Inhibit Deoxyxholic Acid-Induced Apoptosis by Modulating Mitochondrial Transmembrane Potential and Reactive Oxygen Species Production", Molecular Medicine (1998) 4: 165-178.

Invernizzi et al., "Ursodeoxycholate inhibits induction of NOS in human intestinal epithelial cells and in vivo", Am J Physiol (1997) 273:G131-138.

Keith D. Lindor, M.D., "Ursodiol For Primary Sclerosing Cholangitis", The New England Journal of Medicine, (1997) vol. 336, No. 10., pp. 691-695.

Binek et al., "Bedeutung von Ursodeoxycholsäure bei der Eradikation von *Helicobacter pylori*", Schweitz Med Wochenschr (1996) 126 (Suppl. 79): 44S-46S.

Crosignani, et al., "Clinical Pharamcokinetics of Therapeutic Bile Acids", Clin. Pharmacokinet, (1996) vol. 30, No. 5 pp. 333-358.

Han et al., "The Interaction of pH, Bile and *Helicobacter pylori* May Explain Duofenial Ulcer", American Journal of Gastroenterology (1996) vol. 91, No. 6, pp. 1135-1137.

Mohler et al., "Effect of Ursodeoxycholic Acid on HCV Replication in Subtyped Chronic Hepatitis C", Digestive Diseases and Sciences, (1996) vol. 41, No. 6 p. 1276.

Newman et al., "Starch", Analytical Profiles of Drug Substances, (1996) Bristol-Myer Squibb Pharmaceutical Research Institute, New Brunswick, NJ, pp. 523-577.

Nishigaki, et al., "Ursodeoxycholic Acid Corrects Defective Natural Killer Activity by Inhibiting Prostaglandin $E_2$ Production in Primary Biliary Cirrhosis", Digestive Diseases and Sciences, (1996) vol. 41, No. 7, pp. 1487-1493.

Panini et al., "The Influence of 2-Hydroxypropyl-β-Cyclodextrin on the Haemolysis Induced by Bile Acids", J. Pharm. Pharmacol., (1996) vol. 48 pp. 641-644.

Tanaka et al., "Ligand-Independent Activation of the Glucocorticord Receptor by Ursodeoxycholic Acid", The Journal of Immunology (1996) 156:1601-1608.

Buckley et al., "Controlled Release Drugs in Overdose Clinical Consideration", Drug Safety (1996) vol. 12, No. 1 pp. 73-84.

Jorgensen et al., "Characterisation of patients with a complete biochemical response to ursodeoxycholic acid", GUT (1995) 36:935-938.

Klumra et al., "A 1-h Topical Therapy for the Treatment of *Helicobacter pylori* Infection", Am. J. Gastercenterol. (1995) vol. 90, No. 1, pp. 60-63.

Lindor et al., "The Combination of Ursodeoxycholic Acid and Methotrexate for Patients with Primary Biliary Cirrhosis: The Results of a Pilot Study", Hepatology (1995) vol. 22, No. 4 pp. 1158-1162.

Rodrigues et al., "The Site-Specific Delivery of Ursodeoxycholic Acid to the Rat Colon by Sulfate Conjugation", Gastroenterology (1995) vol. 109 pp. 1835-1844.

Simoni et al., "Bioavailability Study of a New, Sinking, Enteric-Coated Ursodeoxycholic Acid Formulation", Pharmacological Research (1995) vol. 31, No. 2 pp. 115-119.

P.J. Sinko, "Utility of Pharmacodynamic Measures for Assessing the Oral Bioavailability of Peptides. 1. Administration of Recombinant Salmon Calcitonin in Rats", Journal of Pharmaceutical Sciences, (1995) vol. 84, No. 11, pp. 1374-1378.

A. Benjamin Suttle and Kim L. R. Brouwer, "Regional Gastronintestinal Absorption of Ranitidine in the Rat", Pharmaceutical Research, (1995) vol. 12, No. 9 pp. 1311-1315.

"Pharmaceutical Necessities", Remington: The Science and Practice of Pharmacy, Mack Printing Co., Easton, Pennsylvania (1995) pp. 1409-1410.

Angelin et al., "Effects of Ursodeoxycholic Acid on Plasma Lipids", Scand J. Gastroenterol. (1994) 29 Suppl 204:24-26.

I. Björkhem, "Inborn Errors of Metabolism with Consequences for Bile Acid Biosynthesis: A Minireview", Scand J. Gastroenteral (1994) 29 Suppl. 204:68-72.

A. Björkland and T.H. Totterman, "Is Primary Biliary Cirrhosis an Autoimmune Disease?", Scand J. Gastroenteral (1994) 29 Suppl. 204:32-9.

Boberg et al., "Etiology and Pathogenesis in Primary Sclerosing Cholangitis", Scand J. Gastroenterol (1994) 29 Suppl. 204:47-58.

Cirillo N.W. and F.R. Zwas., "Ursodeoxycholic Acid in the Treatment of Chronic Liver Disease", Am J Gastroenterol (1994) vol. 89, No. 9 pp. 1447-1452.

K. Einarsson, "Effect of Urodeoxycholic Acid on Hepatic Cholesterol Metabolism", Scand J. Gastroenteral (1994) 29 Suppl. 204:19-23.

S. Friman and J Svarik, "A Possible Role of Ursodeoxycholic Acid in Liver Transplantation", Scand J. Gastroenteral (1994) 29 Suppl. 204:62-4.

A.F. Hofmann, "Pharmacology of Ursodeoxycholic Acid, an Enterohepatic Drug", Scand J. Gastroenteral (1994) 29 Suppl. 204:1-15.

U. Leuschner et al., "Ursodeoxycholic Acid Therapy in Primary Biliary Cirrhosis", Scand J. Gastroenteral (1994) 29 Suppl. 204:40-6.

Lindor et al., "Ursodeoxycholic Acid in the Treatment of Primary Biliary Cirrhosis", Gastroenteral (1994) 106:1284-1290.

McLeod et al., "Glucocorticoid-Dextran Conjugates as Potential Prodrugs for Colon-Specific Delivery: Hydrolysis in Rat Gastrointestinal Tract Contents", J. Pharm Sci., (1994) vol. 83, No. 9., pp. 1284-1288.

McLeod et al., "Glucocorticoid-Dextran Conjugates as Potential Prodrugs for Colon-Specific Delivery: Steady-State Pharamacokinetics in the Rat", Biopharmaceutics & Drug Disposition, (1994) vol. 15, pp. 151-161.

Paumgartner et al., "Ursodeoxycholic Acid Treatment of Cholesterol Gallstone Disease", Scand J. Gastroenterol (1994) 29 Suppl 204: 28-31.

Poupon, et al., "Ursodiol For the Long-Term Treatment of Primary Billary Cirrhosis", The New England Journal of Medicine, (1994) vol. 330, No. 19, pp. 1342-1347.

Roda et al., "Improved Intestinal Absorption of an Enteric-Coated Sodium Ursodeoxycholate Formulation", Pharmaceutical Research, (1994) vol. 11, No. 5 pp. 642-647.

Roda et al., "Influence of Ursodeoxycholic Acid on Biliary Lipids", Scand J Gastroenterol (1994) 29 Suppl. 204:16-8.

A. Stiehl, "Ursodeoxycholic Acid Therapy in Treatment of Primary Sclerosing Cholangitis", Scand J Gastroenterol (1994) 29 Suppl. 204:59-61.

Strandvik et al., "Cystic Fibrosis: Is Treatment with Ursodeoxycholic Acid of Value?", Scand J Gastroenterol (1994) 29 Suppl. 204:65-7.

McLeod et al., "Synthesis and Chemical Stability of Glucocoritcoid-Dextran Esters: Potential Prodrugs for Colon-Specific Delivery", International J. of Pharmaceutics, (1993) vol. 92 pp. 105-114.

Gerrit H. P. Te Wierik et al., "Preparation, Characterization, and Pharmaceutical Application of Linear Dextrins, I. Preparation and Characterization of Amylodextrin, Metastable Amylodextrins, and Metastable Amylose", Pharmaceutical Research, (1993) vol. 10, No. 9 pp. 1274-1279.

Gerritt H. P. Te Wierik et al., "Preparation, Characterization, and Pharmaceutical Application of Linear Dextrins. II. Complexation and Dispersion of Drugs with Amylodextrin by Freeze-Drying and Kneading", Pharmaceutical Research, vol. 10, No. 9 pp. 1280-1284, 1993.

G. H. P. Te Wierik et al., "Preparation, Characterization and Pharmaceutical Application of Linear Dextrins: IV. Drug Release from Capsules and Tablets Containing Amylodextrin", International J. of Pharmaceutics, (1993) vol. 98 pp. 219-224.

Scott L. Myers et al., "Solid-State Emulsions: The Effects of Maltodextrin on Microcrystalline Aging", Pharmaceutical Research, (1993) vol. 10, No. 9 pp. 1389-1391.

Dressman et al., "Gastrointestinal Parameters that Influence Oral Medications", J. of Pharmaceutical Sciences, (1993) vol. 82, No. 9 pp. 857-872.

Thorsteinn Loftsson et al., "The Effect of Cyclodextrins on the Solubility and Stability of Medroxyprogesterone Acetate and Megestrol Acetate in Aqueous Solution", International J. of Pharmaceutics, (1993) vol. 98 pp. 225-230.

Beuers et al., "Ursodeoxycholic Acid for Treatment of Primary Sclerosing Cholangitis: A Placebo-controlled Trial", Hepatology. (1992) vol. 16, No. 3, pp. 707-714.

Bode et al., "Polymorphism in *Helicobacter pylori* —a key function in recurrence of infection", Medizinische Klinik, , (1992) 87(4):179-84.

Colombo et al., "Ursodeoxycholic Acid Therapy in Cystic Fibrosis-associated Liver Disease: A Dose-response Study", Hepatology, (1992) vol. 16, No. 4 pp. 924-930.

De Caprio et al., "Bile Acid and sterol solubilization in 2-hydroxypropyl-ᴣ-cyclodextrin", Journal of Lipid Research, (1992) vol. 33, pp. 441-443.

Fried et al., "Ursodeoxycholic Acid Treatment of Refractory Chronic Graft-versus-Host Disease of the Liver", Annals of Internal Medicine, (1992) 116:624-629.

Walker et al., "Intestinal Absorpotion of Ursodeoxycholic Acid in Patients With Extrahepatic Biliary Obstruction and Bile Drainage", Gastroenterology (1992) 102:810-815.

M.L. Hanninen, "Sensitivity of *Helicobacter pylori* to Different Bile Salts", Eur. J. Clin. Microbiol. Infect., (1991) vol. 10, pp. 515-518.

Mathai et al., "The effect of bile acids on the growth and adherence of *Helicobacter pylori*", Aliment Pharmacol Therap. (1991) 5, pp. 653-668.

Rolandi et al., "Effects of ursodeoxycholic acid (UDCA) on serum liver damage indices in patients with chronic active hepatitis", Eur J. Clin Pharmacol (1991) 40:473-476.

Tan et al., "Studies on Complexation between β-Cyclodextrin and Bile Salts", International J. Pharmaceutics, (1991) vol. 74 pp. 127-135.

G. Buck, "*Campylobacter pylori* and Gastrroduodenal Disease". Clinical Microbiology Reviews, (1990) vol. 3, No. 1 pp. 1-12.

Chazouilleres et al., "Ursodeoycholic Acid for Primary Sclerosing Cholangitis", J. Hepatology, (1990) vol. 11 pp. 120-123.

Colombo et al., "Effects of Ursodeoxycholic Acid Therapy for Liver Disease Associated with Cystic Fibrosis", J. of Pediatrics, (1990) vol. 117, No. 3 pp. 482-489.

M.Y. Morgan, "Branched Chain Amino Acids in the Management of Chronic Liver Disease Facts and Fantasies", J. of Hepatology, (1990) vol. 11 pp. 133-141.

Podda et al., "Effect of Different Doses of Ursofeoxycholic Acid in Chronic Liver Disease", Digestive Diseases and Sciences, (1989) vol. 34, No. 12, Suppl. pp. 59S-65S.

Aigner A and Bauer A, "Bile acids, Long known active substances with a future", Med Monatsschr Pharm (1988) (11): 369-75.

Dioguardi et al., "The role of oral branched-chain amino acids (BCAAs) in the elevation of plasma ammonia (pNH$_3$)", Chapter 68, in Advances in Ammonia Metabolism and Hepatic Encephalopathy, Soeters et al., eds., (1988) Elsevier Science Publishers B.V., pp. 527-533.

Montanari et al., "Oral administration of branched-chain amino acids (BCAAs) in liver cirrhosis (LC): effect on their intra- and extracellular pools", Chapter 67, in Advances in Ammonia Metabolism and Hepatic Encephalopathy, Soeters et al., eds., (1988) Elsevier Science Publishers B.V., pp. 519-526.

N.F.H. Ho, "Utilizing Bile Acid Carrier Mechanisms to Enhance Liver an Small Intestine Absorption", Annals New York Academy of Sciences, (1987) 507:315-29.

Fiaccadori et al., "The effect of dietary supplementation with branch-chain amino acids (BCAAs) vs. casein in patients with chronic recurrent portal systemic encephalopathy: a controlled trial", pp. 489-497. (1988) Elsevier Science Publishers B.V. Advances in ammonia metabolism and hepatic encephalopathy.

D.S. Tompkins and AP West. "*Campylobacter pylori*, acid and bile", J. Clin. Pathol. (1987) 40:1387.
Van Caekenberghe et al., "In Vitro Synergistic Activity between Bismuth Subcitrate and Various Antimicrobial Agents against Campylobacter pylorids", Antimicrobial Agent and Chemotherapy, (1987) vol. 31, No. 9, pp. 1429-1430.
Miyajima et al., "Interaction of β-Cyclodextrin with Bile Salts in Aqueos Solutions", Chem. Pharm. Bull., (1986) vol. 34, No. 3 pp. 1395-1398.
Golub et al., "Physiologic Considerations in Drug Absorption from the Gastrointestinal Tract", J. Allergy Clin. Immunol., (1986) vol. 78, No. 4, Part 2 pp. 689-694.
Gordon et al., "Nasal Absorption of Insulin: Enhancement by Hydrophobic Bile Salts", Proc. Natl. Acad. Sci., (1985) vol. 82 pp. 7419-7423.
Parquet et al., "Bioavailability, Gastrointestinal Transit, Solubilization and Faecal Excretion of Ursodeoxycholic Acid in Man", European J. of Clinical Investigation, (1985) vol. 15 pp. 171-178.
Stefaniwsky et al., "Ursodeoxycholic Acid Treatment of Bile Reflux Gastritis", Gastroenterology (1985)vol. 89, pp. 1000-1004.
K. Müller, "Structural Aspects of Bile Salt-Lecithin Mixed Micelles", Hepatology, (1984) vol. 4, No. 5 pp. 134S-137S.
Murakami et al., "Effect of Bile Salts on the Rectal Absorption of Sodium Ampicillin in Rats", Chem. Pharm. Bull., (1984) vol. 32, No. 5 pp. 1948-1955.
Zentler-Munro et al., "Effect of Intrajejunal Acidity on Aqueous Phase Bile Acid and Lipid Concentrations in Pancreatic Steatorrhoea Due to Cystic Fibrosis", GUT (1984) vol. 25 pp. 500-507.
Moses et al., "Insulin Administered Intranasally as an Insulin-Bile Salt Aerosol Effectiveness and Reproducibility in Normal and Diabetic Subjects", Diabetes, (1983) vol. 32 pp. 1040-1047.
Ziv et al., "Bile Salts Facilitate the Absorption of Heparin from the Intestine", Biochemical Pharmacology, (1983) vol. 32, No. 5 pp. 773-776.
Armstrong et al., "The Hydrophobic-Hydrophilic Balance of Bile Salts. Inverse Correlation between Reverse-Phase High Performance Liquid Chromatographic Mobilities and Micellar Cholesterol-Solubilizing Capacities", J. Lipid Research, (1982) vol. 23 pp. 70-80.
Podda et al., "Gallstone Dissolution After 6 Months of Ursodeoxycholic Acid (UDCA): Effectiveness of Different Doses", J. Int. Med. Res., (1982) vol. 10 pp. 59-63.
Hirai et al., "Effect of Surfactants on the Nasal Absorption of Insulin in Rats", International J. of Pharmaceutics, (1981) vol. 9 pp. 165-172.
Hirai et al., "Mechanisms for the Enhancement of the Nasal Absorption of Insulin by Surfactants", International J. Phamaceutics, (1981) vol. 9 pp. 173-184.
Hollander et al., "Intestinal Absorption of Aspirin, Influence of pH, Taurocholate, Ascorbate and Ethanol", J. Lab. Clin. Med., (1981) vol. 98, No. 4 pp. 591-595.
Reynier et al., "Comparative Effects of Cholic, Chenodeoxycholic, and Ursodeoxycholic Acids on Micellar Solubilization and Intestinal Absorption of Cholesterol", J. Lipid Research, (1981) vol. 22 pp. 467-473.
Igimi et al., "pH-Solubility Relations of Chenodeoxycholic and Ursodeoxycholic Acids: Physical-Chemical Basis for Dissimilar Solution and Membrane Phenomena", J. Lipid Research, (1980) vol. 21 pp. 72-90.
Carey et al., "Micelle Formation by Bile Salts", Arch Intern Med, (1972) vol. 130, pp. 506-527.
CN Office Action; Application No. 200580028815.X; pp. 10, Mar. 13, 2009.
Isreali Office Action; Application No. 181434; pp. 12, Mar. 22, 2009.
CN Office Action; Application No. 200480044467.0; pp. 7, Mar. 27, 2009.
CN Office Action; Application No. 200580034884.1; pp. 6, Mar. 27, 2009.
Hofmann et al.; "Bile Acid Solubility and Preperation in Vitro and in Vivo: The Role of Conjugation, pH, and Ca2+ Ions"; Journal of Lipid Research, vol. 33; pp. 617-626, 1992.
Kimura et al.; "A Case of Cerebrotendinous Xanthomatosis: Effects of Ursodeoxycholic Acid Administration on Serum Bile Acids and Cholestanol"; Jap J Med, vol. 21, No. 3; pp. 210-215, Jul. 1982.
Ribatti et al.; "Development of the Blood-Brain Barrier: A Historical Point of View"; The Anotomical Record (Part B: New Anat.); pp. 6, 2006.
Ota et al.; "Metabolism of Bile Acids IV. Absorption, Distribution, Excretion, and Metabolism of Orally Administered Ursodeoxycholic Acid in Rats"; Hiroshima Journal of Medical Sciences, vol. 26, No. 4; pp. 233-251, Dec. 1977.
MacWalter et al.; "A Benefit-Risk Assessment of Agents Used in the Secondary Prevention of Stroke"; Drug Safety; vol. 25, No. 13; pp. 943-963, 2002.
Wardlaw et al.; "Thrombolysis for Acute Ischaemic Stroke"; Cochrane Database of Systematic Views; Issue 3; pp. 98, 2003.
International Preliminary Report on Patentability; PCT/US2006/036325; pp. 8, Mar. 26, 2009.
Chinese Office Action; Application No. 200580037307.8; pp. 6, May 15, 2009.
European Office Action; Application No. 05 792 858.2-2123; pp. 4, May 20, 2009.
Japanese Office Action (w/translation); Application No. 2000-560868; pp. 10, Oct. 9, 2009.
European Office Action; Application No. 05 813 305.9-1216; pp. 16, Jan. 19, 2010.
Kathleen Parfitt: "Martindale: The Complete drug reference, 32nd edition", Pharmaceutical Press, London, UK, pp. 629-630 (Zalcitabine), Jan. 1, 1999.
Kathleen Parfitt: "Martindale: The Complete drug reference, 32nd edition", Pharmaceutical Press, London, UK, pp. 607-609 (Didanosine), Jan. 1, 1999.
Kathleen Parfitt: "Martindale: The Complete drug reference, 32nd edition", Pharmaceutical Press, London, UK, pp. 556-558 (Paclitaxel), Jan. 1, 1999.
Kathleen Parfitt: "Martindale: The Complete drug reference, 32nd edition", Pharmaceutical Press, London, UK, pp. 513-515 (Cisplatin) Jan. 1, 1999.
Kathleen Parfitt: "Martindale: The Complete drug reference, 32nd edition", Pharmaceutical Press, London, UK, pp. 593 (Sumarin), Jan. 1, 1999.
Mitsuyoshi H et al.; "Ursodeoxycholic acid protects hepatocytes against oxidative injury via induction of antioxidants"; Biochemical and Biophysical Research Communications, vol. 263, No. 2; pp. 537-542, ISSN: 0006-291X, Sep. 24, 1999.
Sun Ah Park et al.; "Cisplatin-induced apoptotic cell death in mouse hybrid neurons is blocked by antioxidants through suppression of cisplatin-mediated accumulation of p53 but not of Fas/Fas ligand"; Journal of Neurochemistry, vol. 75, No. 3; pp. 946-953; ISSN: 0022-3042, 2000.
PCT Notification of Transmittal of the International Search Report and Written Opinion PCT/US2006/008925, 10 pages, Mailing Date Jul. 21, 2006.
Ruf; "Alcohol, Wine and Platelet Function"; Biol. Res., vol. 37; pp. 209-215, 2004.
Renaud et al.; "Effects of Alcohol on Platelet Functions"; Clinica Chimica Acta, vol. 246; pp. 77-89, 1996.
Singh et al.; "The Gastric Ulcer Protective Effect of Boswellic Acids, A Leukotriene Inhibitor From Boswellia serrata, In Rats"; Phytomedicine, vol. 15; pp. 408-415, 2008.
Lazzaroni et al.; "Gastrointestinal Side-Effects of Traditional Non-Steroidal Anti-Inflammatory Drugs and New Formulations"; Ailment Pharmacol Ther, vol. 20; pp. 48-58, 2004.
Fiorucci et al.; "NSAIDs, Coxibs, CINOD and H2S-Releasing NSAIDs: What Lies Beyond the Horizon"; Digestive and Liver Disease, vol. 39; pp. 1043-1051, 2007.
Straube et al.; "Mortality With Upper Gastrointestinal Bleeding and Perforation: Effects of Time and NSAID use"; BMC Gastroenterology, vol. 9, No. 41; pp. 7, 2009.
Ishikawa et al.; "Incidence of Serious Upper Gastrointestinal Bleeding in Patients Taking Non-Steroidal Anti-Inflammatory Drugs in Japan"; Acta Med. Okayama, vol. 62, No. 1; pp. 29-36, 2008.
Lazzaroni et al.; "COXIB and Non-Selective NSAIDs in the Gastroenterological Setting: What Should Patients and Physicians do?"; Digestive and Liver Disease, vol. 39; pp. 589-596; 2007.
Tenenbaum; "The Epidemiology of Nonsteroidal Anti-inflammatory Drugs"; Can J Gastroenterol, vol. 13, No. 2; pp. 119-122, Mar. 1999.

Whittle; "Gastrointestinal Effects of Nonsteroidal Anti-Inflammatory Drugs"; Fundamental & Clinical Pharmacology, vol. 17; pp. 301-313, 2003.
Hsu et al.; "Effect of Sesame Oil on Acidified Ethanol-Induced Gastric Mucosal Injury in Rats"; Journal of Parental and Enteral Nutrition, vol. 33; pp. 6, 2009.
Gonçalves et al.; "Preliminary Studies on Gastric Anti-Ulcerogenic Effects of Averrhoa carambola in Rats"; Acta Farm. Bonaerense, vol. 25, No. 2; pp. 245-247, 2006.
Dokmeci et al.; "L-carnitine Inhibitors Ethanol-Induced Gastric Mucosal Injury in Rats"; Pharmacological Reports, vol. 57; pp. 481-488, 2005.
Barreto et al.; "Gastric Damage Caused by Acidified Ethanol: Role of Molecular HCI"; Am. J. Physiol., vol. 265; pp. 133-137, 1993.
Melo et al.; "Comparison of the Gastroprotective Effect of a Diterpene Lactone Isolated from Croton cajucara with its Synthetic Derivatives"; vol. 87; pp. 169-174, 2003.
Nishida et al.; "YM022 {(R)-1[2,3-dihydro-1-('-methylphenaccyl)-2-oxo-5-phenyl-1H-1,4-benzodiazepin-3-yl]-3-(3-methylphenyl)urea}, A potent and Selective Gastrin/Cholecystokinin-B Receptor Antagonist, Prevents Gastric and Duodenal Lesions in Rats"; The Journal of Pharmacology and Experimental Therapeutics, vol. 270, No. 3; pp. 1256-1261, 1994.
Nørdgård et al.; "COX-2-selective Inhibitors and the Risk of Upper Gastrointestinal Bleeding in High-Risk Patients With Previous Gastrointestinal Diseases: A Population-Based Case-Control Study"; Aliment Pharmacol Ther., vol. 19; pp. 817-825, 2004.
Arora et al.; "Upper Gastrointestinal Bleeding: Etiology and Management"; Indian Journal of Pediatrics, vol. 69; pp. 155-168, Feb. 2002.
Rainsford et al.; "Gastrointestinal Damage and Bleeding From Nonsteroidal Anti-inflammatory Drugs. I. Clinical and Epidemiological Aspects"; Inflammopharmacology, vol. 3; pp. 169-190, 1995.
Fadul et al.; "Perforation of the Gastrointestinal Tract in Patients Receiving Steroids for Neurologic Disease"; Neurology, vol. 38; pp. 348-352, 1988.
Nielsen et al.; "Risk of Hospitalization Resulting from Upper Gastrointestinal Bleeding Among Patients Taking Corticosteroids: A Register-Based Cohort Study"; Am J Med, vol. 111; pp. 541-545, 2001.
Hernandez-Diaz et al.; "Steroids and Risk of Upper Gastrointestinal Complications"; American Journal of Epidemiology, vol. 153, No. 11; pp. 1089-1093, 2001.
Nielsen et al.; "Upper gastrointestinal Bleeding in Patients Taking Corticosteroids"; JCOM, vol. 9, No. 1; pp. 1, Jan. 2002.
XP 002337365, Jul. 8, 1987, XP (abstract).
Kirk et al; "Inclusion Compounds"; Encyclopedia of Chemical Technology, Fourth Edition; vol. 14 pp. 125-135, 1995.
XP 002337364, Oct. 7, 1988, XP (abstract).
XP 002337367, Feb. 1, 1994, XP (abstract).
XP 002337363, May 10, 1998, XP (abstract).
M.C. Allwood et al.; "Stability of Ampicillin Infusions in Unbuffered and Buffered Saline"; International Journal of Pharmaceutics, vol. 97; pp. 219-224, 1993.
Higginbottom et al., International Journal of Pharmaceutics, vol. 109, pp. 173-180, 1994.
PCT International Search Report and Written Opinion, PCT/US2004/039507, 29 pages, Mailing Date Oct. 25, 2005.
Thao et al.; "Antibacterial and anti-atrophic effects of a highly soluble, acid stable UDCA formula in Helicobacter pylori-induced gastritis"; Biochemical Pharmacology; BCP-9750; pp. 12, 2008.
"Saccharide Composition Typical Carbohydrate Profiles" GPC Technical Bulletin TB30-021296, Grain Processing Corp. (1 page), 1999.
Carey, MD et al. "Micelle Formation by Bile Salts Physical-Chemical and Thermodynamic Considerations" Arch. Intern. Med., vol. 130 (pp. 506-527), Oct. 1972.
Hollander et al. "Intestinal Absorption of Aspirin Influence of pH, Taurocholate, Ascorbate and Ethanol" J. of Lab. Clin. Med., vol. 98, No. 4 (pp. 591-595), Oct. 1980.
Hirai et al. "Mechanisms for the Enhancement of the Nasal Absorption of Insulin by Surfactants" International J. of Pharmaceutics, vol. 9 (pp. 173-184), 1981.

Reynier et al. "Comparative Effects of Cholic, Chenodeoxycholic, and Ursodeoxycholic Acids on Micellar Solubilization and Intestinal Absorption of Cholesterol" J. of Lipid Research, vol. 22 (pp. 467-473), 1981.
H.P.R. Bootsma et al.; "β-Cyclodextrin as an Excipient in Solid Oral Dosage Forms: in Vitro and in Vivo Evaluation of Spray-Dried Diazepam-β-Cyclodextrin Products"; Inernation Journal of Pharmaceutics, vol. 51; pp. 213-223, 1989.
Mollan, Jr. et al. "On of Aqueous Soluble Starch Conversion Products" Maltodextrin (pp. 308-349), 1995.
Nagamatsu "Phase I Clinical Study of Ursodesoxycholic Acid" Jpn. Pharmacol. Ther. vol. 22, No. 6 (pp. 145-159), 1997.
"Maltrin Maltodextrins & Corn Syrup Solids Chemical and Physical Properties" GPC Technical Bulletin, TB31-021296, Grain Processing Corp. (Brochure + 4 pages), 1999.
PCT International Search Report PCT/US2004/039507, (12 pages), Mailing Date May 8, 2005.
International Search Report and Written Opinion for International Application No. PCT/US2006/036325 (13 pages), Jun. 4, 2007.
International Preliminary Report on Patentability and Written Opinion for International Application No. PCT/US2004/039507 (21 pages), Jun. 7, 2007.
Igimi et al. "ph-Solubility Relations of Chenodeoxycholic and Ursodeoxycholic Acids: Physical-Chemical Basis for Dissimilar Solution and Membrane Phenomena" J. of Lipid Research, vol. 21 (pp. 72-90), 1980.
The American Heritage Dictionary, Second College Edition, Houghton Mifflin Company, pp. 1213, 1982.
Takeda et al., "Prevention of Irinotecan (CPT-11)-Induced Darrhea by Oral Alkalization Combined with Control of Defecation in Cancer Patients" International Journal of Cancer, vol. 92, pp. 269-275, 2001.
Schuldes et al., "Reversal of Multidrug Resistance and Increase in Plasma Membrane Fluidity in CHO Cells with R-Verapamil and Bile Salts", European Journal of Cancer vol. 37, pp. 660-667, 2001.
Chemical Abstracts Registry Entry 191595-91-2, "Bamet R2" American Chemical Society, Copyright 2007.
Communication pursuant to Article 94(3) EPC; Application No. 05 813 305.9-1216; pp. 7, Mar. 7, 2008.
Database WPI Section Ch, Week 198824 Derwent Publications Ltd., London, GB, AN-1988-165730 XP002337363 & JP 63104925 A, 1988.
Database WPI Section Ch, Week 198846 Derwent Publications Ltd., London, GB, AN-1988-327783 XP002337364 & JP 63243031 A, 1988.
Cannon et al. "Reduction of pain on intravenous infusion with bile salt formulations for a macrolide antibiotic" International Journal of Pharmaceutics, vol. 114, No. 1 (pp. 65-74), Jul. 13, 1994.
Villaneuva et al. "Effect of Bile Acids of Hepatobiliary Transport of Cisplatin by Perfused Rat Liver" Pharmacology and Toxicology, vol. 80, No. 3 (pp. 111-117), Sep. 26, 1996.
Dominguez et al. "Low in Vivo Toxicity of a Novel Cisplatin-Ursodeoxycholic Derivative (Bamet-UD2) with Enhanced Cytostatic Activity versus Liver Tumors" Journal of Pharmacology and Experimental Therapeutics, vol. 297, No. 3 (pp. 1106-1112), Jan. 16, 2001.
Rodrigues et al. "Neuroprotection by a Bile Acid in an Acute Stroke Model in the Rat" Journal of Cerebral Blood Flow & Metabolism, vol. 22 (pp. 463-471), 2002.
Drug Name: Tauroursodeoxycholic Acid (TUDCA), TUDCA-Various/UDCA (Ursodiol-Actigall, Watson Pharmacceuticals, Novartis, Generics), 7 pages, 2004.
Chemical Abstracts Registry Entry 64480-66-6, "Glycoursodeoxycholic Acid ", American Chemical Society, Copyright 2007.
International Search Report and Written Opinion for International Application No. PCT/US2005/037211 (16 pages), Feb. 13, 2007.
International Preliminary Report on Patentability for International Application No. PCT/US2005/037211 (10 pages), Apr. 26, 2007.
European Office Action for Application No. 04 812 094.3, 8, Applicant: Seo Hong Yoo, 8 pages, Dec. 17, 2007.
Brazilian Office Action for Patent Application PI 9912395-9, 6 pages, Dec. 5, 2008.

G.D. Ghadge et al.; "Mutant Superoxide Dismutase-1-Linked Familial Amyotrophic Lateral Sclerosis: Molecular Mechanisms of Neuronal Death and Protection"; The Journal of Neuroscience, vol. 17, No. 22; pp. 8756-8766, Nov. 15, 1997.

C.M.P. Rodrigues et al.; "Bilirubin and Amyloid-β Peptide Induce Cytochrome c Release Through Mitochondrial Membrane Permeabilization"; Molecular Medicine, vol. 6, No. 11; pp. 936-946, 2000.

C.D. Keene et al.; "A Bile Acid Protects Against Motor and Cognitive Deficits and Reduces Striatal Degeneration in the 3-Nitropropionic Acid Model of Huntington's Disease"; Experimental Neurology, vol. 171; pp. 351-360, 2001.

C.M.P. Rodrigues et al.; "The Therapeutic Effects of Ursodeoxycholic Acid as an Anti-Apoptotic Agent"; Expert Opin. Investig. Drugs, vol. 10, No. 7; pp. 1243-1253, 2001.

Tanahashi et al., "Treatment of Acute Ischemic Stroke: Recent Progress" Internal Medicine vol. 41, pp. 337-344, 2002.

Ikeda et al., "Antioxidant Nutrients and Hypoxia/Ischemia Brain Injury in Rodents", Toxicology vol. 189, pp. 55-61, 2003.

Ma et al. "Ursodeoxycholic acid inhibits endothelin-1 production in human vascular endothelial cells" European Journal of Pharmacology, vol. 505 (pp. 67-74), 2004.

Chu et al. "Human neural stem cells improve sensorimotor deficits in the adult rat brain with experimental focal ischemia" Brain Research 1016 (pp. 145-153), 2004.

International Search Report and Written Opinion; PCT/US2005/039089; pp. 15, Mailed: May 24, 2006.

EMEA/CHMP/EWP Workshop; "Slowing the Progression of Neurodegenerative Diseases: Medicinal Productions (MP) Clinical Development"; European Medicines Agency, Pre-authorisation Evaluation of Medicines for Human Use; http://www.emea.europa.eu; pp. 15, Oct. 2, 2006.

International Preliminary Report on Patentability and Written Opinion for International Application No. PCT/US2005/030679 (9 pages), Mar. 6, 2007.

27th Annual Meeting of the Korean Neurological Association; "Oral Presentation"; Journal of the Korean Neurological Association; vol. 26, Suppl. 2; pp. 3, 2008.

Chinese Office Action for Patent Application 01804549.9, 6 pages, Oct. 30, 2008.

European Office Action for Application No. 05 820 886.9, 3 pages, Nov. 14, 2008.

Y. Hattori, et al.; "Ursodeoxycholic Acid Inhibits the Induction of Nitric Oxide Synthase"; European Journal of Pharmacology; pp. 147-150, 1996.

Deborah F. Gelinas; "Riluzole"; ALS and Other Motor Neuron Disorders,(Suppl 4); pp. 3-4, 2000.

D. Lapenna et al.; "Antioxidant Properties of Ursodeoxycholic Acid"; Biochemical Pharmacology, vol. 64; pp. 1661-1667, 2002.

N. Shibata et al.; "Molecular Biological Approaches to Neurological Disorders Including Knockout and Transgenic Mouse Models"; Neuropathology, vol. 22; pp. 337-349, 2002.

E. Diguet et al.; "Effects of Riluzole on Combined MPTP + 3-Nitropropionic Acid-Induced Mild to Moderate Striatonigral Degeneration in Mice"; Journal of Neural Transmission; pp. 19, 2004.

R.E. Castro et al.; "The Bile Acid Tauroursodeoxycholic Acid Modulates Phosphorylation and Translocation of Bad via Phosphatidylinositol 3-Kinase in Glutamate-Induced Apoptosis of Rat Cortical Neurons"; American Society for Pharmacology and Experimental Therapeutics; pp. 34, Jun. 9, 2004.

L. Dupuis et al.; "Evidence for Defective Energy Homeostasis in Amyotrophic Lateral Sclerosis: Benefit of a High-Energy Diet in a Transgenic Mouse Model"; www.pnas.org/cgi/doi/10.1073/pnas.0402026101 ; PNAS, Jul. 27, 2004, vol. 101, No. 30, pp. 11159-11164.

International Preliminary Report on Patentability for International Application No. PCT/US2005/039089 (9 pages), May 10, 2007.

Examination Report form Australian Patent Application No. 2005295541 dated Jul. 27, 2010, 2 pages.

Israeli Office Action and translation; Israeli Patent Application No. 181434; pp. 4, Sep. 5, 2010.

* cited by examiner

BILE PREPARATIONS FOR GASTROINTESTINAL DISORDERS

CROSS-REFERENCE TO RELATED APPLICATIONS

This application is a continuation-in-part of U.S. application Ser. No. 11/251,137 filed Oct. 14, 2005, no U.S. Pat. No. 7,772,220 which claims the benefit of U.S. Provisional Application Ser. No. 60/619,199 filed Oct. 15, 2004, both of which are incorporated herein by reference in their entirety.

This application is also a continuation-in-part of U.S. application Ser. No. 09/778,154 filed Feb. 5, 2001, now U.S. Pat. No. 7,303,768 which claims the benefit of U.S. Provisional Application No. 60/180,268 filed Feb. 4, 2000, and is a continuation-in-part of U.S. application Ser. No. 09/357,549 filed Jul. 20, 1999, now U.S. Pat. No. 6,251,428, which claims the benefit of U.S. Provisional Application No. 60/094,069 filed Jul. 24, 1998.

TECHNICAL FIELD

The present disclosure is related to clear aqueous solutions of one or more bile acids that may be used to ameliorate one or more symptoms of a gastrointestinal disorder.

BACKGROUND OF THE DISCLOSURE

The full therapeutic value of some pharmaceutical compounds (e.g., medications, drugs) may be difficult to realize due to off-setting unwanted or adverse effects (e.g., toxic effects). In some cases, one or more unwanted or adverse effects of a pharmaceutical may be so significant, that the agent cannot be used safely in humans using other formulations. In other cases, dosages may have to be limited to avoid an unwanted or adverse effect. In still other cases, the course of therapy may have to be shortened. In addition, exigent circumstances or life-threatening illnesses may compel patients to simply endure such unwanted or adverse effects to gain a pharmaceutical compound's benefits.

Ulcerative lesions of the gastrointestinal tract are one of the major side effects associated with the use of alcohol, non-steroidal anti-inflammatory drugs (NSAIDs) and gastric irritating drugs (e.g., antibiotics, adrenal corticoid steroids, anticancer drugs). Accumulation of neutrophils and/or oxygen free radicals and/or inhibition of prostaglandins may play a significant role in the mechanism of gastrointestinal lesions induced by ethanol, NSAIDS, and gastric irritating drugs.

Oral administration of high concentrations of ethanol (i.e., 75-100%) and/or oral administration of moderate concentrations of acidic ethanol may be extremely damaging to gastrointestinal epithelium (e.g., in rats). Such concentrations or combinations may be used to induce damage experimentally to investigate the efficacy of various gastrointestinal protective agents against the use of alcohol, short- or long-term NSAIDS, and/or gastric irritating drugs. Lower doses of ethanol (e.g., about 40% to about 50%) may be less toxic, particularly if administered in a non-acid medium. For example, exposure of the gastroduodenal mucosa to a 50% ethanol solution may cause only mild damage macroscopically to the glandular portion of the stomach. Similarly, exposure of the gastroduodenum to 150 mM HCl may cause no visible damage to the gastroduodenal mucosa. In contrast, administration of about 50% ethanol in 150 mM HCl may lead to severe macroscopic injury involving as much as 20% of the glandular mucosa. In fact, a solution of 50% ethanol in 150 mM HCl may be as severely damaging as absolute ethanol alone or 750 mM HCl alone. Thus relatively small amounts of HCl and a moderate concentration of ethanol have a synergistic effect that greatly exacerbates the gastroduodenal injury one would expect from the activity of these agents alone.

Ingestion of high concentrations of ethanol may result in hemorrhagic gastritis characterized by mucosal edema, subepithelial hemorrhages, cellular exfoliation and inflammatory cell infiltration. Hemorrhagic gastritis usually coexists with duodenal erosive lesions like edema and vacuole. Ingestion of moderate concentrations of ethanol may affect the mucosal barrier and histology. Morphologically, alcohol-induced gastroduodenal superficial injury may involve the inter-foveolar epithelium and gastroduodenal pits, and may heal rapidly by restitution. On the other hand, deeper lesions associated with ingestion of high concentrations of ethanol may involve intramucosal hemorrhage and vascular engorgement. As a consequence of damage to microvessels, leakage of inflammatory mediators may occur, and vasoconstriction of submucosal arteries may result in ischemia. Eventually, these events may lead to severe necrotic mucosal injury.

NSAIDs, which may include drugs with analgesic, antipyretic and/or anti-inflammatory effects, are widely used. Gastrointestinal toxicity may be observed as gastrointestinal mucosal damage like acute hemorrhagic erosions as well as small bowel and colon injury. Small intestinal damage may be observed as ulceration, perforation, and stricture, particularly following long term administration of NSAIDs. Patients receiving NSAIDs long-term may further display enteropathy including intestinal inflammation, acute blood loss, protein loss, and/or vitamin B12 or bile acid malabsorption. NSAIDs may also induce mucosal damage of the large intestine. Compromise of the colon may include de novo NSAID induced colitis, reactivation of quiescent colitis, and/or lower gastrointestinal bleeding from diverticular disease.

SUMMARY

Therefore, a need has arisen for methods and compositions that ameliorate or eliminate unwanted and/or adverse gastrointestinal effects associated with consumption and/or administration of alcohol, NSAIDs, and/or gastric irritating drugs. An adverse gastrointestinal effect may include, without limitation, esophageal damage, acid sensitivity of gastrointestinal mucus, gastroduodenal mucosal cell death, gastrointestinal necrosis, gastrointestinal apoptosis, gastroduodenal mucosal lesion, gastroduodenal mucosal erosion, gastroduodenal ulcer, gastrointestinal cancer, gastrointestinal bleeding, perforation, epigastralgia, gastritis, gastrointestinal redness, gastrointestinal edema, malabsorption, intestinal dysmotility, colitis, and combinations thereof.

The present disclosure relates to methods and compositions that may ameliorate or eliminate a toxicity (e.g., a gastrointestinal effect) of a compound. For example, a method of ameliorating or eliminating a gastrointestinal effect of a compound may include co-administering the compound and a bile acid composition. A compound may, in some embodiments, be selected from the group consisting of alcohol (e.g., ethanol), an NSAID, a gastric irritating drug, and combinations thereof. In some embodiments, co-administration may include administering both the pharmaceutical compound and a bile acid in a single composition. It may also include simultaneous administration of a plurality of compositions. Alternatively, coadministration may include administration of a plurality of compositions at different times during the same period (e.g., at different times on the same day).

In some embodiments, the present disclosure provides compositions which include (1) a bile acid, a bile acid derivative, a bile acid salt, or a bile acid conjugated with an amine, (2) water, and (3) a sufficient quantity of an aqueous soluble starch conversion product such that the bile acid and the starch conversion product remain in solution at any pH within a selected pH range.

The disclosure further relates to a composition which comprises (1) a bile acid, a bile acid derivative, a bile acid salt, or a bile acid conjugated with an amine, (2) water, and (3) a sufficient quantity of an aqueous soluble non-starch polysaccharide such that the bile acid and the polysaccharide remain in solution at any pH within a selected pH range.

The disclosure further relates to a pharmaceutical composition which comprises (1) a bile acid, a bile acid derivative, a bile acid salt, and/or a bile acid conjugated with an amine, (2) water, and/or (3) a sufficient quantity of an aqueous soluble starch polysaccharide such that the bile acid in the polysaccharide remain in solution in any pH within a selected pH range.

The disclosure further relates to a pharmaceutical composition which comprises (1) a bile acid, a bile acid derivative, a bile acid salt, or a bile acid conjugated with an amine, (2) water, (3) a pharmaceutical compound in a pharmaceutically appropriate amount and/or (4) a sufficient quantity of an aqueous non-starch conversion product and/or an aqueous non-starch polysaccharide such that the bile acid, the pharmaceutical compound and the carbohydrate remain in solution at any pH within a selected pH range. According to a non-limiting embodiment of the disclosure, a pharmaceutical compound may be selected from the group consisting of alcohol, an NSAID, a gastric irritating drug, and combinations thereof.

The disclosure further relates to solution dosage forms of bile acid compositions. These dosage forms may have improved bioavailability and absorbability of a bile acid. In embodiments in which these compositions further contain a pharmaceutical compound, these compositions may also have improved bioavailability and/or absorbability of the pharmaceutical compound.

In some embodiments of the disclosure, a composition is provided which comprises (1) a bile acid, a bile acid derivative, a bile acid salt, or a bile acid conjugated with an amine, (2) water, and/or (3) a sufficient quantity of carbohydrate such that the bile acid component and the carbohydrate remain in solution at any pH within a selected pH range, wherein the carbohydrate is a combination of an aqueous soluble starch conversion product and an aqueous soluble non-starch polysaccharide. In embodiments containing both soluble non-starch polysaccharide and high molecular weight starch conversion product, the amounts of each are such that when combined together in the composition they are sufficient to allow the bile acid component, the high molecular weight starch conversion product, the soluble non-starch polysaccharide and the pharmaceutical compound, if any, to remain in solution at any pH within a selected pH range.

According to some embodiments of the disclosure, a composition may include an aqueous solution that is substantially free of precipitates and particles. An aqueous solution may include (a) a first material selected from the group consisting of a bile acid, an aqueous soluble derivative of a bile acid, a bile acid salt, and a bile acid conjugated with an amine by an amide linkage; (b) a carbohydrate selected from the group consisting of an aqueous soluble starch conversion product or an aqueous soluble non-starch polysaccharide; and (c) water, wherein the first material and the carbohydrate both remain in solution for all pH values obtainable in an aqueous system. In some embodiments, the condition of an aqueous solution being free of precipitates and/or particles may be a result of formulation the formulation itself, the method of making the composition, and/or other factors. The condition of an aqueous solution being free of precipitates and/or particles may be a result of something other than a filtration step and/or heating above ambient temperature in some embodiments. A composition according to some embodiments of the disclosure may protect at least a portion of a subject's gastrointestinal tract from a noxious or otherwise harmful composition.

In some embodiments of the disclosure, a combination therapy composition is provided which may increase the intensity of a response to or efficacy of a pharmaceutical compound. Such a composition may permit administration of lower dosages of a pharmaceutical compound, attack a disease complex at different points, affect elimination and/or alter absorption of a pharmaceutical compound. Such a composition may lead to or contribute to a reduction in toxicity and/or side effects of a pharmaceutical.

BRIEF DESCRIPTION OF THE DRAWINGS

The patent application file contains at least one drawing executed in color. Copies of this patent or patent application publication with color drawing(s) will be provided by the United States Patent and Trademark Office upon request and payment of the necessary fee.

Some specific example embodiments of the disclosure may be understood by referring, in part, to the following description and the accompanying drawings, wherein.

DETAILED DESCRIPTION

Figure 1A:
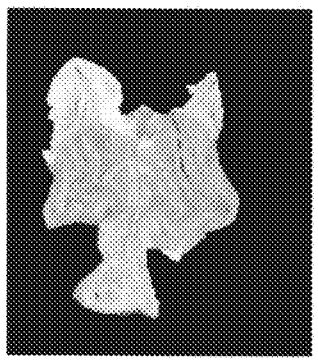
FIG. 1A (upper left image) shows a gastric hemorrhagic region and duodenal lesion which were induced by intragastric administration of one milliliter of acidic ethanol solution A to a rat. Solution A (1 mL) was given intragastrically 30 minutes prior to administration of acidic ethanol solution A.

Therapeutic benefits of a pharmaceutical compound may be mitigated or even negated if that agent also displays toxicity. Alcohol, NSAIDs and gastric irritating drugs may have desirable and/or therapeutic value. However, their use may be limited due to gastrointestinal effects that may occur upon administration of these agents. For example, without being limited to any particular mechanism of action, excessive ethanol may increase super oxide anion and hydroxyl radical production and lipid peroxidation in the gastro duodenal mucosa. Lipid peroxidation may be mediated by the interaction of hydroxyl radicals with the cell membrane. This may produce lipid-derived free radicals such as conjugated dienes and lipid hydroperoxides extracellularly and/or intracellularly. These radicals may be extremely reactive products and may cause oxidative damage. For example, these products may produce mitochondrial permeability transition and mitochondrial depolarization, which precede apoptotic cell death in gastroduodenal mucosal cells. Acute administration of absolute ethanol to rats may produce gastro duodenal mucosal lesions and erosions similar to those occurring in gastroduodenal ulcer. Moreover, chronic alcohol consumption and heavy smoking may be major risk factors for cancer of the upper aerodigestive tract (e.g., oropharynx, hypopharynx, larynx and/or oesophagus). Alcoholic liver cirrhosis may also be a precancerous condition. Chronic alcohol ingestion even at moderate dosage may enhance carcinogenesis in the colorectum and/or breast, especially in individuals with increased susceptibility to developing cancer. Acetaldehyde may be carcinogenic, mutagenic, may bind to DNA and/or protein, may degrade folate and produce secondary hyperregeneration and may be predominantly responsible for alcohol associated carcinogenesis. Acetaldehyde may be produced by various alcohol dehydrogenases in the liver and/or in the gastrointestinal tract and/or by gastrointestinal bacteria. Acetaldehyde may be degraded by acetaldehyde dehydrogenases to acetate. Synthesis and degradation of acetaldehyde may be modulated in part by polymorphisms and/or mutations of the genes that encode the enzymes in catabolism and/or anabolism.

NSAIDs may be associated with unwanted and/or adverse gastrointestinal effects. Without being limited to any particular mechanism of action gastrointestinal toxicity, for example, may be mediated by both a non-prostaglandin induced local injury and/or systemic inhibition of cyclooxygenase (COX). This may lead to a subsequent reduction in the cytoprotective prostaglandins required for effective mucosal defense. Again, without being limited to any particular mechanism drug induced changes in local eicosanoid metabolism may be coupled with a topical toxic effect. Together these may induce a subsequent increase in the permeability of the mucosa to toxins and luminal antigens such as bile, pancreatic secretion, and bacteria. Enterohepatic recirculation of NSAIDs may be important for this effect.

NSAIDs may induce necrosis and/or apoptosis depending on the treatment conditions. For example, short-term treatment of cells with high concentrations of NSAIDs and long-term treatment of cells with low concentrations of NSAIDs may induce necrosis and apoptosis, respectively. In some embodiments, an NSAID may be indomethacin. Short-term exposure of cells to indomethacin may rapidly decrease cell viability in vitro in a dose-dependent manner (e.g. using primary cultures of guinea pig gastric mucosal cells).

Gastrointestinal mucosa may resist continual onslaught of aggressive agents such as alcohol, NSAIDs and gastric irritating drugs. This resistance, without being limited to any particular mechanism, may be mediated by neuronal modulating processes such as the release of vasodilator mediators. Interactions between endothelium-derived vasodilator mediators, including those prostaglandins may regulate gastrointestinal mucosal microcirculation and integrity. Endothelial cells may also release highly labile humoral vasodilator substances, including for example nitric oxide (NO). NO may mediate vascular relaxation induced by vagal stimulation. However, production of NO from a calcium-independent (inducible) form of the enzyme may lead to cell injury in the endothelium. Thus, induction of NO synthesis may not always be beneficial. For example, formation and interaction between superoxide and NO radicals may be important elements of oxidative challenges in gastrointestinal mucosa. An inflammatory reaction may be initiated and/or amplified by a proinflammatory mediator. A proinflammatory mediator may be released from injured tissues and/or synthesized during an inflammatory reaction. These substances may result in further local tissue injury by release and activation of destructive enzymes and/or production of oxygen-derived free radicals. Thus, without being limited to any particular mechanism of action, removal of oxygen-derived free radicals may stimulate healing of ethanol-induced acute gastroduodenal mucosal injury. Activation of polymorphonuclear leukocytes and macrophages, may result in increased superoxide generation and/or production of NO by inducible NO synthase. Gastritis in animals may lead to a significant increase in the inducible enzyme NO synthase. This in turn may result in production of NO which may react with oxygen or superoxide to yield more reactive oxidants, such as peroxynitrite. Secondary oxidants such as these may be responsible for most biological oxidative damage, and may be a target of antioxidant defense. One or more endogenous proinflammatory mediators may be activated during exposure to noxious agents and/or severe tissue trauma. For example, leukotriene C4 may act as a proinflammatory mediator and lead to microcirculatory disturbances and severe mucosal tissue injury.

Gastroduodenal bleeding may be caused by acute gastroduodenal mucosal lesion. Acute gastroduodenal mucosal lesion may be indicated where a patient displays sudden onset of epigastralgia, epigastric discomfort, vomiting, hematemesis and melena following probable causes. Diagnosis may be facilitated by endoscopy upon findings of gastroduodenal erosion, hemorrhagic gastritis and duodenal ulcer. There are a variety of causes for acute gastroduodenal mucosal lesion including, for example, psychological and physical stress, exposure to NSAIDs, exposure to gastric irritating drugs, alcohol abuse, serious organ failure (e.g. liver, kidney, heart, anisakiasis and combinations thereof). There may also be a variety of endoscopic findings of acute gastroduodenal mucosal lesion including, for example, redness, edema, erosion, ulcer and bleeding. These may vary quickly. The key to management may be prevention; however, once established, hemorrhagic gastritis may be treated with both supportive measures and measures directed toward healing the mucosal damage.

Ursodeoxycholic acid (3α-7β-dihydroxy-5β-cholanic acid) ("UDCA") may be useful as a pharmaceutical compound for the treatment of and the protection against many types of disease (e.g., liver disease). UDCA, which is hydrophilic, may be present in normal human bile at a low concentration (e.g., about 3% by weight of total bile acids). UDCA may be administered to a subject displaying one or more cholestatic disorders, radiolucent gall stones, biliary dyspepsia, primarily biliary cirrhosis, primary sclerosing cholangitis, intrahepatic cholestasis of pregnancy, cystic fibrosis-associated liver disease, pediatric liver disorder, and chronic graft-versus-host disease of the liver, chronic active hepatitis, hepatitis C, and combinations thereof.

In spite of the extremely valuable therapeutic activities and medical uses of bile acids as therapeutically active agents and as carriers and/or adjuvants, commercial use of bile acids has been limited to pharmaceutical formulations in which the bile acid is present in a solid form (e.g., tablets, capsules, and suspensions). This may be due to the insolubility of bile acids in aqueous media at pH from approximately 1 to 8. Bile has an extremely bitter taste and an equally bitter after-taste that lasts several hours both of which may be due to bile's insolubility. The few aqueous dosage forms that are available are unstable, and have very limited uses because of pH control and maintenance problems. Moreover, some commercial pharmaceutical dosage forms of bile acids have been shown to have scant bioavailability.

The present disclosure provides, in some embodiments, clear, stable solutions of soluble bile acids that offset, ameliorate or alleviate the toxicity of an agent. A solution of the disclosure may be used, for example, as a delivery vehicle for a pharmacological agent with one or more unwanted and/or adverse gastrointestinal effects. Alternatively, a solution of the disclosure may be used alone to offset, ameliorate or alleviate one or more unwanted and/or adverse gastrointestinal effects of an agent (e.g., alcohol) to which a subject is separately exposed. Solutions of the disclosure may be administered separately, in terms of both the route and time of administration, relative to the agent associated with the one or more unwanted and/or adverse gastrointestinal effects to be offset, ameliorated, and/or eliminated. In some embodiments of the disclosure, a bile composition blocks a toxic effect mediated by an oxidative process.

In some embodiments, a bile acid composition of the disclosure may lack one or more of the disadvantageous features of existing commercial dosage forms of UDCA. A bile acid composition of the disclosure may, in some embodiments, contact a gastrointestinal lesion without any precipitation and may function as a locally acting drug in the gastrointestinal tract. Bile acid dosage forms, according to some embodiments of the disclosure, may be suitable or adaptable for oral and/or parenteral administration. In some embodiments, a bile acid composition of the disclosure may include an intact molecule of UDCA and an aqueous soluble starch conversion product (e.g., a product resulting from hydrolysis of starch). A bile acid composition, according to some embodiments of the disclosure, may include solubilized bile acid in water wherein the bile acid remains in aqueous solution without any precipitation at any pH.

The solubility of UDCA in some solutions of the disclosure may be about 3,000 times higher than that of some commercialized forms of UDCA (e.g., 0.15 M vs. 0.05 mM) and may be about 300 times higher than that of TUDCA. In some embodiments, a solution of the disclosure may deliver solubilized UDCA to a subject's stomach, duodenum, jejunum, ileum, colon and/or blood. An oral and/or parenteral dosage form may, in some embodiments, contain, for example, 500 mg of UDCA and may have a Cmax that is at least 8 times higher than an existing commercial UDCA form and a Tmax that is about 4-6 times shorter than an existing commercial UDCA form. A fast Tmax and high Cmax mean that solubilized UDCA may be absorbed from the upper stomach very efficiently. For example, absorbed solubilized UDCA may cross the gastric mucosa.

A solution of the disclosure may be used, in some embodiments, to protect a subject's gastrointestinal track from the use of alcohol, an NSAID and/or a gastric irritating drug. For example, a solution of the disclosure may be administered in connection with administration of a pharmaceutical compound that is associated with an unwanted or adverse gastrointestinal effect, such as an NSAID and/or a gastric irritating drug.

An NSAID, according to some embodiments of this disclosure, may include a Salicylate (e.g., aspirin, methyl salicylate and diflunisal). An arylalkanoic acid (e.g., indomethacin, sulindac and diclofenac), 2-arylpropionic acid (e.g., (profens)ibuprofen, ketoprofen, naproxen and ketorolac), an N-arylanthranilic acid (fenamic acids) (e.g., mefenamic acid), an oxicam (e.g., piroxicam, meloxicam, coxibscelecoxib rofecoxib, valdecoxib, parecoxib and etoricoxib) and a sulphonanilide (e.g., nimesulide). In some embodiments, a gastric irritating drug may include an anti-cancer drug selected from the group consisting of aminoglutethimide, anastrazole, bicalutamide, chlorambucil, cyclophosphamide, cytarabine, dacarbazine, flutamide, letrozole, lomustine, mercaptopurine, methotrexate, nilutamide, plicamycin, procarbazine HCl, tacrolimus hydrate, and adrenal corticoid steroid. A gastric irritating drug, in some embodiments may include cortisol, cortisone, prednisone, prednisolone, desoxycorticosterone acetate, methylprednisolone, triamcinolone, fluprednisolone, bethamethasone, dexamethasone, fludrocortisone and combinations thereof.

Without being limited to any particular mechanism of action, a hydrophobic bile acid salt may induce apoptosis in the liver of a subject. Coadministration of a hydrophobic bile salt and UDCA may inhibit hepatocyte apoptosis in vivo. Both in hepatocytes and in nonhepatic cells apoptosis may be induced with various factors including, for example, hydrophobic acids, ethanol, transforming growth factor-α, an agonistic Fas antibody, and/or okadaic acid. In some embodiments, UDCA may attenuate apoptosis and display cytoprotection without being limited to any particular mechanism of action. UDCA may have this affect by modulating mitochondrial membrane perturbation, Bax translocation and/or cytochrome c release.

Pharmacological action of UDCA may include replacement and/or displacement of toxic bile acids through UDCA in a dose-dependent manner, cytoprotective effects in a dose-dependent manner, stabilization/protection of cell membranes in a dose-dependent manner, antiapoptotic effects in a dose-dependent manner, immunomodulatory effects due to activation of the intracellular glucocorticoid receptor in a dose-dependent manner, antiinflammatory effects due to repression of NF-kB and inhibition of the induction of nitric oxide synthase, stimulation of bile secretion in a dose-dependent manner, Stimulation of exocytosis and insertion of canalicular membrane transporters in a dose-dependent manner.

UDCA is practically insoluble at pH 1 to 8. The solubility of its protonated form is about 0.05 mM. The solubility of its taurine conjugated metabolite (TUDCA; 0.45 mM) is about ten times higher than UDCA solubility. Moreover, TUDCA is the only bile acid (BA) with relatively low solubility when protonated. Following oral administration, approximately 30 to 60% of UDCA is absorbed along the length of the jejunum and ileum by nonionic passive diffusion and is absorbed in the ileum by active transport mechanisms and to a small extent (20% of an ingested dose) in the colon due to the insolubility of crystal UDCA, which causes extremely slow and incomplete dissolution due to the low aqueous solubility of its non-ionized molecules and more lipophilicity than the ionized bile salt species, and can therefore partition into biological membranes.

Once taken up by hepatocytes, UDCA may be conjugated to TUDCA and GUDCA, the latter two being the secreted bile acids in humans and excreted in bile by hepatic first-pass clearance. Consequently, its blood levels are extremely low in the systemic circulation. Bile acids undergo extensive hepatic recycling, or free UDCA may also be secreted by hepatocytes in bile, where it may be actively and efficiently reabsorbed by cholangiocytes. UDCA and GUDCA are absorbed by both active and passive transport mechanisms, while tauro-conjugated UDCA (TUDCA) may be transported actively in the terminal ileum.

In some embodiments, a UDCA dose above 10±12 mg/kg per day may not further increase its proportion in bile since a large quantity of UDCA may be biotransformed to CDCA through 7-keto-lithocholic acid by intestinal bacteria. Alternatively, UDCA may be converted to CDCA by epimerization of the 7β-hydroxyl group and further to lithocholic acid (LCA). Therefore, with increasing doses of UDCA the absorption of UDCA decreases.

In some embodiments, administration of a composition of the disclosure may achieve adequate amounts of solubilized UDCA in lesions caused by NSAIDS, alcohol and gastric irritating drug at the gastrointestinal tract, and/or in the systemic circulation to have a therapeutic effect. A solution of the disclosure may, in some embodiments, display significantly increased aqueous solubility of UDCA, increased membrane permeability, protection from epimerization of UDCA to CDCA.

Without being limited to any particular mechanism of action, the present disclosure provides clear, stable solutions of solubilized bile acids that may protect gastrointestinal tract from necrosis and/or apoptosis by the use of NSAIDs, alcohol and gastric irritating drug (antibiotics, adrenal corticoid steroid, anti-cancer drug).

Bile acids may act as intracellular signaling agents, which modulate cellular transport, alter intracellular $Ca^{2+}$ levels, and activate cell surface receptors. Ursodeoxycholic acid (UDCA) is a hydrophilic bile acid with proven clinical efficacy in the treatment of hepatobiliary disorders. UDCA may be rapidly conjugated with glycine or taurine in vivo to produce glycoursodeoxycolic and tauroursodeoxycholic (TUDCA) acids, respectively. UDCA and its derivatives and conjugates may function as cytoprotective agents by inhibiting apoptosis.

The present disclosure relates to an aqueous solution comprising (i) one or more soluble bile acids, aqueous soluble bile acid derivatives, bile acid salts, or bile acid conjugated with an amine, (collectively "bile acid"), (ii) water, and (iii) one or more aqueous soluble starch conversion products or aqueous soluble non-starch polysaccharides in an amount sufficient to produce a solution which does not form a precipitate at any pH within a desired pH range. The composition may contain a bile acid or a bile acid salt which itself has pharmaceutical effectiveness. Formulations of the disclosure may act as a carrier, an adjuvant or enhancer for the delivery of a pharmaceutical material which remains dissolved in the composition of the disclosure across the desired pH range. Alternatively, according to some embodiments of the disclosure, the composition may comprise a non-bile acid pharmaceutical that is incompletely soluble.

In some embodiments, it may be an advantage of this disclosure that the bile acid and the carbohydrate remain in solution without precipitation at any pH from acidic to alkaline. These aqueous solution systems of bile acid are substantially free of precipitate or particles. A further advantage of this disclosure is that the aqueous solution systems demonstrate no changes in physical appearance such as changes in clarity, color or odor following the addition of strong acids or alkali even after several months (e.g., 1, 2, 3, 4, 5, 6, 7, 8, 9, 10, 11, or 12 months) observation under accelerated conditions of storage at 50° C.

In some embodiments of the disclosure, an aqueous solution system of a bile acid is administered orally whereupon it reaches the gastrointestinal track without precipitation of bile acids by exposure to acidic gastric juices and alkaline juices of the gastrointestinal track. These solubilized bile acid formulations demonstrate intact solution systems in the intestine can be effectively and completely absorbed by the direct contact between solubilized bile acid and intestine and, consequently, undergo enterohepatic cycling. According to an embodiment of the disclosure, bile acid solubility (e.g. precipitation and changes in physical appearance) is affected by whether a carboxylic acid side chain of certain bile acids can be protonated (non-ionized; in acidic stomach), is ionized (in small intestine), or is a simple carboxylic acid (in cell).

The ionization state of a bile acid carboxylic acid side chain may affect the hydrophobicity and the hydrophilicity of the bile acid in some aqueous solution systems. In some embodiments of the disclosure, that ionization state is manipulated by adjusting the pH to control the toxicity, absorption, and amphiphilicity of bile acids. One or more bile acids may be dissolved in these aqueous solution systems as a therapeutically active agent, as an adjuvant of a drug, as a carrier of a drug or as an enhancer of drug solubility. These aqueous solution systems may be prepared for oral consumption, mouthwashes, gargles, nasal preparations, otic preparations, injections, douches, enemas, topical skin preparations, other topical preparations, and cosmetic preparations which have a desired pH without the disadvantage of precipitation or deterioration in physical appearance after long periods of time.

Soluble bile acids are any type of aqueous soluble bile acids. A bile acid salt is any aqueous soluble salt of a bile acid. Bile salts exhibit greater solubilizing capacity for phospholipid and cholesterol and are consequently better detergents. More hydrophobic bile salts may be more injurious to various membranes, both in vivo and in vitro. Aqueous dissolved salts of bile acids may be formed by the reaction of bile acids described above and an amine including but not limited to aliphatic free amines such as trientine, diethylene triamine, tetraethylene pentamine, and basic amino acids such as arginine, lysine, ornithine, and ammonia, and amino sugars such as D-glucamine, N-alkylglucamines, and quaternary ammonium derivatives such as choline, heterocyclic amines such as piperazine, N-alkylpiperazine, piperidine, N-alkylpiperidine, morpholine, N-alkylmorphline, pyrrolidine, triethanolamine, and trimethanolamine. According to some embodiments of the disclosure, soluble bile acid salts may also include aqueous soluble metal salts of bile acids, bile acid/cyclodextrin inclusion compounds, and aqueous soluble O-sulfonated bile acids.

Soluble bile acid derivatives, according to some embodiments of this disclosure, may be those derivatives which are as soluble in aqueous solution as or more soluble in aqueous solution than is the corresponding underivatized bile acid. Bile acid derivatives include, but are not limited to derivatives formed at the hydroxyl and carboxylic acid groups of the bile acid with other functional groups including but not limited to halogens and amino groups. Soluble bile acid may include an aqueous preparation of a free acid form of bile acid combined with one of HCl, phosphoric acid, citric acid, acetic acid, ammonia, or arginine.

Bile acids that may be used in accordance with the teachings of this disclosure include, without limitation, ursodeoxycholic acid, chenodeoxycholic acid, cholic acid, hyodeoxycholic acid, deoxycholic acid, 7-oxolithocholic acid, lithocholic acid, iododeoxycholic acid, iocholic acid, tauroursodeoxycholic acid, taurochenodeoxycholic acid, taurodeoxycholic acid, taurolithocholic acid, glycoursodeoxycholic acid, taurocholic acid, glycocholic acid, and their derivatives at a hydroxyl or carboxylic acid group on the steroid nucleus.

In some embodiments, administration of a composition of the disclosure may result in higher in vivo levels of bile acids than at least some existing commercial preparations. Therefore, the therapeutic potential of bile acid may be more fully achieved than other formulations. In vivo levels of bile acids attainable with existing formulations in which bile is incompletely solubilized may be lower and require administration of larger amounts of bile acids. Completely dissolving all or substantially all bile according to some embodiments of the disclosure, by contrast, may permit higher in vivo levels of bile acid to be achieved, even though the same or lower doses are administered.

In some embodiments of the disclosure, a plurality of bile acids may be used in a single formulation. Mixtures of two or more bile salts of differing hydrophobic activity may behave as a single bile salt of an intermediate hydrophobic activity. As a result, detergent properties and the toxicity of mixtures of two bile acids of differing hydrophobic activity often are intermediate between the individual components.

Mixtures of two or more bile salts of differing hydrophobic activity may behave as a single bile salt of an intermediate hydrophobic activity. As a result, detergent properties and the toxicity of mixtures of two bile acids of differing hydrophobic activity often are intermediate between the individual components.

Carbohydrates suitable for use in the disclosure include aqueous soluble starch conversion products and aqueous soluble non-starch polysaccharides. According to some embodiments of the present disclosure, aqueous soluble starch conversion products include carbohydrates obtained from the partial or incomplete hydrolysis of starch under various pH conditions. Non-limiting examples include maltodextrin, dextrin, liquid glucose, corn syrup solid (dried powder of liquid glucose), and soluble starch, (e.g., maltodextrin or corn syrup solid). In some embodiments, MALTRIN® M200, a corn syrup solid, and MALTRIN® M700, a maltodextrin, may be used. MALTRIN® M200 and MALTRIN® M700 are manufactured by GPC®, Grain Processing Corporation of Muscatine. For the purpose of this embodiment, the term "corn syrup" may include both corn syrup and liquid glucose.

In some embodiments, aqueous soluble starch conversion products arise from only hydrolytic and/or catabolic activity on starch. A starch conversion product may, in some embodiments, include at least one reducing end and/or at least one non-reducing end. If it is polymeric, it may be linear or branched. The molecular weight may be from about 100 mass units to over 106 mass units. High molecular weight aqueous soluble starch conversion products are those having a molecular weight over 105.

According to some embodiments of the present disclosure, aqueous soluble non-starch polysaccharides may be formed under various pH conditions by various hydrolytic or synthetic mechanisms. Non-limiting examples include to dextran, guar gum, pectin, indigestible soluble fiber. If polymeric, the polymer has at least one reducing end and/or at least one non-reducing end. The polymer may be linear or branched. The molecular weight may be from about 100 mass units to over 106 mass units. For example, the molecular weight is over 105 mass units.

In some embodiments, cyclodextrin, the formation of which involves a condensation step that eliminates its free ends, may be regarded as neither an aqueous soluble starch conversion product nor an aqueous soluble non-starch polysaccharide. In some embodiments, a composition of the disclosure may be substantially free of cyclodextrin. In some embodiments, a composition of the disclosure may be completely free of cyclodextrin. Alternatively, in some embodiments of the disclosure, a formulation a composition of the disclosure may comprise cyclodextrin in addition to a starch conversion product and/or a non-starch polysaccharide.

The amount of high molecular weight aqueous soluble starch conversion product and/or soluble non-starch polysaccharide used in embodiments of the disclosure is at least the amount needed to render the bile acid(s) in the preparation soluble over the concentration and/or pH range desired.

In some embodiments of the disclosure, the approximate minimal weight ratio of maltodextrin to UDCA required to prevent UDCA precipitation may be 6:1 (i.e. 1.2 g for every 0.2 g of UDCA, 6 g for every 1 g of UDCA, and 12 g for every 2 g of UDCA in 100 mL of water).

In some embodiments of the disclosure, the approximate minimal quantity of maltodextrin may be 30 g for every 200 mg of chenodeoxycholic acid, 12 g for every 200 mg of 7-ketolithocholic acid, 10 g for every 200 mg of cholic acid and 50 g for every 200 mg of deoxycholic acid.

In some embodiments of the disclosure, the approximate minimal weight ratio of liquid glucose (commercial light corn syrup) to UDCA required to prevent the precipitation of bile acids from the aqueous solution dosage forms of the disclosure may be about 25:1 (i.e. 12.5 g for every 500 mg UDCA in 100 mL water and 25 g for every 1 g ursodeoxycholic acid in 200 mL water).

In some embodiments of the disclosure, the approximate minimal quantity of dried powder of liquid glucose (corn syrup solid, e.g. MALTRIN® M200) required to prevent the precipitation of bile acids from the aqueous solution dosage forms of the disclosure is 30 g for every 1 g ursodeoxycholic acid in 100 mL water, and approximately 60 g for every 2 g of ursodeoxycholic acid in 200 mL water.

In some embodiments of the disclosure, the approximate minimal quantity of soluble non-starch polysaccharide required to prevent the precipitation of bile acids from the aqueous solution dosage forms of the disclosure may be 50 g guar gum for every 500 mg ursodeoxycholic acid in 100 mL water and 80 g of pectin for every 500 mg of ursodeoxycholic acid in 100 mL water. The minimal required quantity of high molecular weight aqueous soluble starch conversion products and/or soluble non-starch polysaccharide, according to some embodiments, may be primarily determined by the absolute quantity of bile acids in the solution formulation rather than the concentration.

In some embodiments of the disclosure, the formulation further comprises dietary fiber. Non-limiting examples of dietary fiber include guar gum, pectin, psyllium, oat gum, soybean fiber, oat bran, corn bran, cellulose and wheat bran.

In some embodiments of the disclosure, the formulation further comprises emulsifying agents. For the purpose of the disclosure, the term "emulsifying agent" includes emulsifying agents and suspending agents. Non-limiting examples of emulsifying agents include guar gum, pectin, acacia, carrageenan, carboxymethyl cellulose sodium, hydroxymethyl cellulose, hydroxypropyl cellulose, methyl cellulose, polyvinyl alcohol, povidone, tragacanth gum, xanthan gum, and sorbian ester.

The selected pH range for which the formulation will not precipitate its bile acid, starch conversion product, soluble non-starch polysaccharide or its pharmaceutical compound may be any range of pH levels obtainable with an aqueous system. In some embodiments, the range may be between about pH 1 and about pH 14 and/or between about pH 1 and about pH 10. In some embodiments, a pH range may be any subset of the range of pH levels obtainable in an aqueous system sufficient for a pharmaceutical formulation to remain in solution from preparation, to administration, to absorption in the body, according to the method of administration. Thus, the composition may be used as a pharmaceutical formulation wherein the pharmaceutical compound remains in solution without precipitation at prevailing pH levels in the mouth, stomach and intestines. In some embodiments of the disclosure, a bile acid remains dissolved under acidic conditions as a free bile acid in spite of the general insolubility of bile acids under acidic conditions.

A solution, according to some embodiments, may be administered with one or more pharmaceutical compounds (e.g., a pharmaceutical compound includes hormones, hormone antagonists, analgesic, antipyretics, anti-inflammatory drugs, immunoactive drugs, antineoplastic drugs, antibiotics, anti-inflammatory agents, sympathomimetic drugs, anti-infective drugs, anti-tumor agents, anesthetics, and drug for targeting or affecting liver, cardiovascular system, and respiratory system). Administration of a bile composition of the disclosure with pharmaceutical compound may, in some embodiments, (a) increase the intensity of a response to the pharmaceutical compound, (b) increase the efficacy of the pharmaceutical compound, (c) decrease the required dose of the pharmaceutical compound, and/or (d) decrease the toxicity of the pharmaceutical compound. Solutions of the disclosure may also be administered separately, in terms of both the route and time of administration.

In some embodiments of the disclosure, a bile composition may comprise a pharmaceutical compound including, without limitation, an NSAID and/or a gastric irritating drug. Non-limiting examples of pharmaceutical compounds include insulin, heparin, calcitonin, ampicillin, octreotide, sildenafil citrate, calcitriol, dihydrotachysterol, ampomorphine, yohimbin, trazodone, acyclovir, amantadine.HCl, rimantadine.HCl, cidofovir, delavirdine.mesylate, didanosine, famciclovir, forscarnet sodium, fluorouracil, ganciclovir sodium, idoxuridine, interferon-α, lamivudine, nevirapine, penciclovir, ribavirin, stavudine, trifluridine, valacyclovir.HCl, zalcitabine, zidovudine, indinavir.$H_2SO_4$, ritonavir, nelfinavir.$CH_3SO_3H$, saquinavir.$CH_3SO_3H$, d-penicillamine, chloroquine, hydroxychloroquine, aurothioglucose, gold sodium thiomalate, auranofin levamisole, dacarbazine, diethyldithiocarbamate, isoprinosine, methyl inosine monophosphate, muramyl dipeptide, diazoxide, hydralazine.HCl, minoxidil, dipyridamole, isoxsuprine.HCl, niacin, nylidrin.HCl, phentolamine, doxazosin.$CH_3SO_3H$, prazosin.HCl, terazocin.HCl, clonidine.HCl, nifedipine, molsidomine, amiodarone, acetylsalicylic acid, verapamil, diltiazem, nisoldipine, isradipine, bepridil, isosorbide.dinitrate, pentaerythrytol.tetranitrate, nitroglycerin, cimetidine, famotidine, nizatidine, ranitidine, lansoprazole, omeprazole, misoprostol, sucralfate, metoclopramide.HCl, erythromycin, bismuth compound, alprostadil, albuterol, pirbuterol, terbutaline.$H_2SO_4$, salmetrol, aminophylline, dyphylline, ephedrine, ethylnorepinephrine, isoetharine, isoproterenol, metaproterenol, n-docromil, oxy triphylline, theophylline, bitolterol, fenoterol, budesonide, flunisolide, beclomethasone.dipropionate, fluticasone.propionate, codeine, codeine sulfate, codeine phosphate, dextromethorphan.HBr, triamcinolone.acetonide, montelukast sodium, zafirlukast, zileuton, cromolyn sodium, ipratropium bromide, nedocromil sodium benzonate, diphenhydramine.HCl, hydrocodone.bitartarate, methadone.HCl, morphine sulfate, acetylcysteine, guaifenesin, ammonium carbonate, ammonium chloride, antimony potassium tartarate, glycerin, terpin.hydrate, colfosceril palmitate, atorvastatin.calcium, cervastatin.sodium, fluvastatin.sodium, lovastatin, pravastatin.sodium, simvastatin, picrorrhazia kurrva, andrographis paniculata, moringa oleifera, albizzia lebeck, adhata vasica, curcuma longa, momordica charantia, gymnema sylvestre, terminalia arjuna, azadirachta indica, tinosporia cordifolia, metronidazole, amphotericin B, clotrimazole, fluconazole, haloprogin, ketoconazole, griseofulvin, itraconazole, terbinafin.HCl, econazole.$HNO_3$, miconazole, nystatin, oxiconazole.$HNO_3$, sulconazole.$HNO_3$, cetirizine.2HCl, dexamethasone, hydrocortisone, prednisolone, cortisone, catechin and its derivatives, glycyrrhizin, glycyrrhizic acid, betamethasone, ludrocortisone.acetate, flunisolide, fluticasone.propionate, methyl prednisolone, somatostatin, lispro, glucagon, proinsulin, insoluble insulins, acarbose, chlorpropamide, glipizide, glyburide, metformin.HCl, repaglinide, tolbutamide, amino acid, colchicine, sulfinpyrazone, allopurinol, piroxicam, tolmetin sodium, indomethacin, ibuprofen, diflunisal, mefenamic acid, naproxen, and trientine.

Additional examples of pharmaceutical compounds that may be included in a formulation may include any compound that remains soluble in the formulation. With an additional pharmaceutical compound in the formulation, a bile acid in solution may act as an adjuvant, carrier, and/or enhancer for the solubility of certain therapeutically active agents, including, but not limited to, insulin (pH 7.4-7.8), heparin (pH 5-7.5), calcitonin, ampicillin, amantadine, rimantadine, sildenafil, neomycin sulfate (pH 5-7.5), apomorphine, yohimbin, trazodone, ribavirin, paclitaxel and its derivatives, retinol, and tretinoin, which are soluble and stable in acid and/or alkali and can be added as needed into these aqueous solution dosage forms of certain concentrations of bile acids in this disclosure. Certain therapeutically active agents, including, but not limited to, metformin HCl (pH 5-7), ranitidine HCl, cimetidine, lamivudine, cetrizine 2HCl (pH 4-5), amantadine, rimantadine, sildenafil, apomorphine, yohimbine, trazodone, ribavirin and dexamethasone, hydrocortisone, prednisolone, triamcinolone, cortisone, niacin, taurine, vitamins, naturally occurring amino acids, catechin and its derivatives, glycyrrhizal extract and its main constituents such as glycyrrhizin and glycyrrhizic acid, water soluble bismuth compounds (e.g., bismuth sodium tartrate), and which are soluble and stable in acid and/or alkali can be added as needed into these aqueous solution dosage formulations containing ursodeoxycholic acid in this disclosure.

Some embodiments of the disclosure may be practiced with pH adjustable agents. Non-limiting examples include HCl, $H_3PO_4$, $H_2SO_4$, $HNO_3$, $CH_3COOH$, citric acid, malic acid, tartaric acid, lactic acid, phosphate, eidetic acid and alkalies.

In some embodiments of the disclosure, a formulation may be used to treat (e.g., ameliorate at least one symptom) human and mammalian diseases. In some embodiments, a composition of the disclosure may be used to treat gastrointestinal disorders, liver diseases, gall stones, and/or hyperlipidemia. Non-limiting examples of gastrointestinal diseases include any disease and/or disorder of the stomach and/or intestine. Additional non-limiting examples of gastrointestinal diseases include any disease and/or disorder that effects the stomach and/or intestine. Non-limiting examples of liver diseases may include alcohol-induced liver diseases and non-alcohol-induced liver diseases. Non-limiting examples of gastrointestinal disorders may include chronic gastritis, reflux gastritis, and peptic ulcer disease. Non-limiting examples of non-alcohol-induced liver diseases may include primary biliary cirrhosis, acute and chronic hepatitis, primary sclerosing cholangitis, chronic active hepatitis, and excess accumulation of fat in the liver.

In some embodiments, a composition of the disclosure may be used to treat viral, bacterial and/or fungal diseases. In some embodiments of the disclosure, a formulation may be administered to treat and/or eradicate *Helicobacter pylori* infection. In some embodiments, a composition of the disclosure may be used to treat and/or eradicate hepatitis C virus infection, influenza A, Influenza C, parainfluenza 1, sendai, rubella, and/or pseudorabies virus.

In some embodiments, a composition of the disclosure may be used to treat an acute and/or chronic inflammatory disease. Non-limiting examples of inflammatory diseases may include bronchitis, chronic pharyngitis, and/or chronic tonsillitis. In some embodiments of the disclosure, a formulation may be administered to treat hypercholersterolemia.

In some embodiments of the disclosure, a composition may be prepared and/or modified such that it may be administered as a liquid, solid, powder or tablet. In some embodiments of the disclosure, a composition may be comprised in a parenteral solution (e.g., an injectable solution, a solution, a syrup, a thick syrup or a paste. A non-limiting example of a syrup is a solution of maltodextrin wherein the concentration of maltodextrin is less than 500 g/L. A non-limiting example of a syrup is a solution of maltodextrin wherein the concentration of maltodextrin is between 500 g/L and 1.0 kg/L inclusive. A non-limiting example of a thick syrup is a solution of maltodextrin wherein the concentration of maltodextrin is between 1.0 kg/L and 1.2 kg/L inclusive. A non-limiting example of a paste is a solution of maltodextrin wherein the concentration of maltodextrin is greater than 1.2 kg/L. Other non-limiting examples of a syrup, a thick syrup, and/or a paste may have a viscosity that is within about ±10% of the foregoing, respective example.

The stability of dosage formulations of the disclosure may be evaluated by measuring the concentration of the relevant bile acid over time in preparations comprising soluble bile acid, a high molecular weight aqueous soluble starch conversion product, and water at various pH and temperature levels. The retention time (high performance liquid chromatography) of each bile acid may be adjusted as needed to permit individual analysis each bile acid present in complex samples, i.e. a sample having a plurality of bile acids. Stability tests may also be performed by assessing the light-scattering properties of a test solution. In addition, established accelerated testing conditions may be used.

In some embodiments, a composition of the disclosure may, without being filtered, remain substantially free of precipitates and particles for over one day, over two days, over three days, over one week, over two weeks, over three weeks, over four weeks, over five weeks, over six weeks, over seven weeks, over eight weeks, over nine weeks, over ten weeks, over eleven weeks, over twelve weeks, over fifteen weeks, over eighteen weeks, over twenty-one weeks, over twenty-four weeks, over nine months, over twelve months, over eighteen months, and/or over twenty-four months. In some embodiments, a composition of the disclosure may have greater than about 95% of the starting bile concentration, greater than about 96% of the starting bile concentration, greater than about 97% of the starting bile concentration, greater than about 98% of the starting bile concentration, and/or greater than about 99% of the starting bile concentration after one day, after two days, after three days, after one week, after two weeks, after three weeks, after four weeks, after five weeks, after six weeks, after seven weeks, after eight weeks, after nine weeks, after ten weeks, after eleven weeks, after twelve weeks, after fifteen weeks, after eighteen weeks, after twenty-one weeks, after twenty-four weeks, after nine months, after twelve months, after eighteen months, and/or after twenty-four months.

All stability tests performed on solutions of the disclosure were satisfactory in that the concentration of bile acid as measured by HPLC did not change appreciably over time at various pH levels. Particularly, all bile acid solution formulations tested showed excellent results in the stability tests with no precipitation and no physical appearance changes over the test period. Some formulations remain stable for over 2 years. The aqueous solution dosage forms according to this disclosure that were tested did not change either physically or chemically at various pH conditions under accelerated conditions despite the addition of therapeutically and chemically active agents that are stable and soluble in hydrochloric acid solution. Therefore, these aqueous solution systems may be useful pharmaceutical dosage forms for therapeutically active bile acids preparations, and/or drug (pharmaceutical compound) delivery preparations. In such preparations, a bile acid may play a role as a drug adjuvant, a drug carrier, or a drug solubility enhancer (e.g., by micelle formation) at various pH conditions without stability problems (e.g., including precipitation in acidic conditions).

Human cells (neuron) were treated with a solution of the disclosure and 50 μM of hydrogen peroxide and/or cisplatin. Hydrogen peroxide may be a strong oxidant. Cisplatin may stimulate production of reactive oxygen species (ROS), which may interfere with antioxidant defense system. Cell viability, cell proliferation, and apoptosis were then analyzed by measurement of MTT reduction. Several studies, using exogenous ROS, and $H_2O_2$, in particular, demonstrate that exposure of human and rat peripheral vascular smooth muscle cells (VSMCs) to relatively low levels of oxidant stress, for short periods promotes cell growth, whereas prolonged exposure to higher concentrations leads to cell death, either by apoptosis or necrosis.

Cell viability for hydrogen peroxide with and without solution of the disclosure was evaluated by using the MTT assay. Cells treated with a solution of the disclosure (0.2 mg/mL solubilized UDCA) and hydrogen peroxide (50 μM) displayed the highest cell viability (75% compared to control, 100%). The lowest cell viability (26% compared to control, 100%) was observed in cells treated with hydrogen peroxide (50 μM) alone. These effects were found in a dosage-dependent fashion.

Cell viability in the presence of cisplatin was evaluated in like manner. The highest cell viability (87% compared to control, 100%) was observed in cells treated with both cisplatin (20 μM) and a solution of the disclosure (1 mg/mL soluble UDCA), whereas the lowest cell viability (35% compared to control, 100%) was observed in cells treated with cisplatin (20 μM) alone. These effects were also found in a dosage-dependent fashion. According to the MTT assays, a solution of the disclosure may block almost completely hydrogen peroxide-induced oxidative cytotoxicity and may completely block cisplatin-induced oxidative cytotoxicity. In conclusion, a composition of the disclosure may possess strong antioxidative properties and non-cytotoxicity.

EXAMPLES

Some embodiments of the present disclosure may be understood in connection with the following examples. However, one skilled in the art will readily appreciate the specific materials, compositions, and results described are merely illustrative of the disclosure, and are not intended to, nor should be construed to, limit the scope disclosure and its various embodiments.

Example 1

Preparation of Bile Acid Solutions

A stock solution of bile acid was prepared by first dissolving UDCA (15 g) in 400 mL NaOH (1.6 g) solution. Next, to the resulting clear solution, 450 g of maltodextrin was added, portion by portion with vigorous agitation. To this resulting solution 100 mL of a preservative solution which contains 0.95 g of methyl p-hydroxybenzoate and 0.3 g of sodium hydrogensulfite was added and then stirred. The volume was then adjusted to 1.0 L with pharmaceutical grade water. Lastly, the resulting clear solution was filtered with proper filtering apparatus to remove foreign substances. Dilutions of this solution to the desired UDCA concentration were prepared:

Solution A; 4 mL of stock solution was diluted with 6 mL of saline to make 10 mL (solubilized UDCA 6 g/L);
Solution B and D; Stock solution (solubilized UDCA 15 g/L);
Solution C; 6 mL of stock solution was diluted with 4 mL of saline to make 10 mL (solubilized UDCA 9 g/L);
Solution E; 2 mL of stock solution was diluted with 8 mL of saline to make 10 mL (solubilized UDCA 3 g/L);
Solution G; 8 mL of stock solution was diluted with 2 mL of saline to make 10 mL (solubilized UDCA 12 g/L); and
Solution H; 6 mL of acidic ethanol was diluted with 4 mL of saline to make 10 mL (solubilized UDCA 6 g/L).

Example 2

Preparation of Acidic Ethanol

Acidic ethanol A (150 mM HCl ethanol); 1.4 mL of 37% hydrochloric acid was added to absolute ethanol to make total 100 mL.
Diluted acidic ethanol B (90 mM HCl ethanol solution); 6 mL of acidic ethanol solution (150 mM HCl ethanol) was diluted with 4 mL of saline to make total 10 mL.

Example 3

Animals

Rats weighing 200-250 g were used in the experiments. They were housed at room temperature and had free access to standard pellet diet for rats and tap water. The rats were deprived of food for 24 h before experimentation, but were allowed free access to drinking water.

Example 4

Gastric Damage Induced by Ethanol

Gastric hemorrhagic lesions were induced by intragastric administration of one milliliter of acidic ethanol A to each rat. Aqueous solutions of a bile acid (Solution A, Solution B, Solution C, Solution D, Solution E, Solution G, and Solution H) or saline were given intragastically 30 min prior to administration of acidic ethanol to each rat. A rat (B) was administered aqueous solutions of a bile acid only. A rat (F) was administered acidic ethanol A only. A rat (H) that is control (+) for hemorrhagic area calculation was administered acidic alcohol B only. A rat (I) that is control (−) for hemorrhagic area calculation was administered saline only. The animals were killed 60 min after the administration of ethanol. The stomach including duodenum of each animal was then removed, opened along the greater curvature, and gently rinsed with physiological saline. Thereafter, the washed stomach was spread and fixed by 3% paraformaldehyde-saline (pH 7.4), and photo scanned using a scanner (Epson Perfection 3200 photo, 2003 yr.). The area of gastric glandular mucosal lesion was measured with an image processing program (TINA version 2.09 gauge, Bioteckh and KAIST, 1993 yr.), in blinded evaluation. Lesion area is expressed as a percentage of total area of the stomach, except for the fundus.

Example 5

Results

Figure 1B:
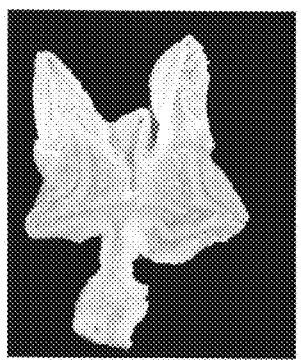
FIG. 1B (upper center image) shows an uninjured gastric and duodenal region following intragastric administration of one milliliter of solution B only to a rat.
Figure 1C:
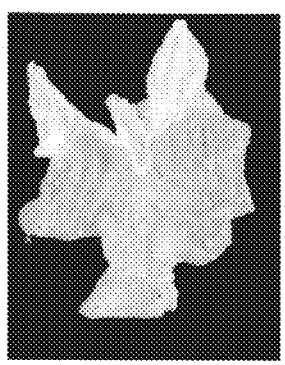
FIG. 1C (upper right image) shows a gastric hemorrhagic region and duodenal lesion which were induced by intragastric administration of one milliliter of acidic ethanol solution A to a rat. Solution C (1 mL) was given intragastrically 30 min prior to administration of acidic ethanol A.
Figure 1D:
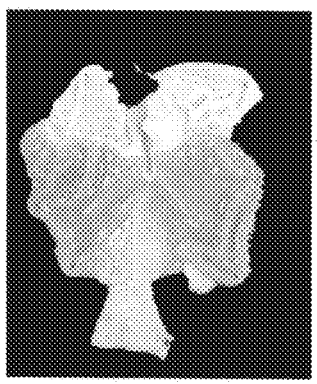
FIG. 1D (middle left image) shows an uninjured gastric and duodenal region following intragastric administration of one milliliter of acidic ethanol solution A to a rat. Solution D (1 mL) was given intragastrically 30 minutes prior to administration of acidic ethanol solution A.
Figure 1E:
FIG. 1E (middle center image) shows a gastric hemorrhagic region and duodenal lesion which were induced by intragastric administration of one milliliter of acidic ethanol solution A to a rat. Solution E (1 mil) was given intragastrically 30 min prior to administration of acidic ethanol A.
Figure 1F:
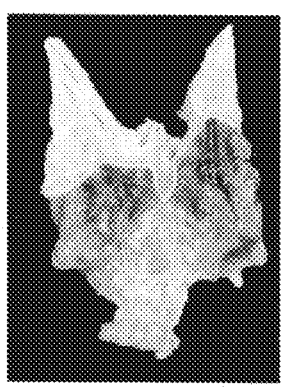
FIG. 1F (middle right image) shows a gastric hemorrhagic region and duodenal lesion induced by intragastric administration of one milliliter of acidic ethanol A only to a rat.
Figure 1G:
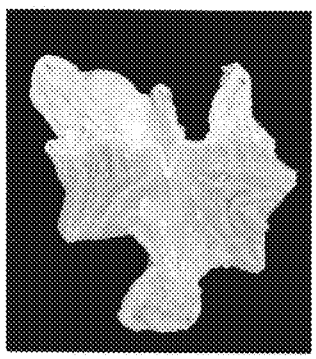
FIG. 1G (lower left image) shows an uninjured gastric and duodenal region following intragastric administration of one milliliter of acidic ethanol solution A to a rat. Solution G (1 mL) was given intragastrically 30 min prior to administration of acidic ethanol A.
Figure 1H:
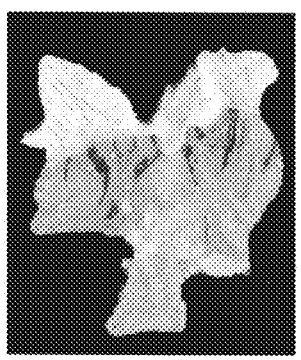
FIG. 1H (lower center image) shows a gastric hemorrhagic region and duodenal lesion which were induced by intragastric administration of one milliliter of diluted acidic ethanol solution B only to a rat.
Figure 1I:
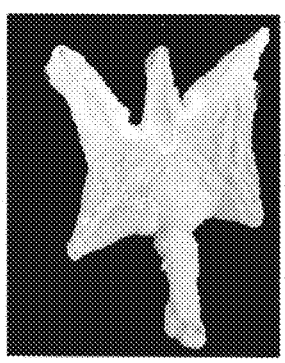
FIG. 1I (lower right image) shows a healthy gastric and duodenal region after intragastric administration of saline only to a rat.

An aqueous solution of solubilized UDCA did not cause any gastro duodenal damage even at the high concentration of UDCA (15 g/L of solubilized UDCA) (FIG. 1B). Acidic alcohol A, by contrast, induced severe hemorrhage on the entire stomach, and severe edema and vacuole on stomach and duodenum (FIG. 1F) in comparison to diluted acidic alcohol B (FIG. 1H). An aqueous solution of solubilized UDCA completely protected gastro intestine from the gastro hemorrhage and duodenal edema and vacuole by almost absolute acidic alcohol (FIG. 1D). An aqueous solution containing lower concentration than solubilized UDCA of stock solution also completely protected gastro intestine from the gastro hemorrhage and duodenal edema and vacuole by almost absolute acidic alcohol (FIG. 1G).

Figure 2A:
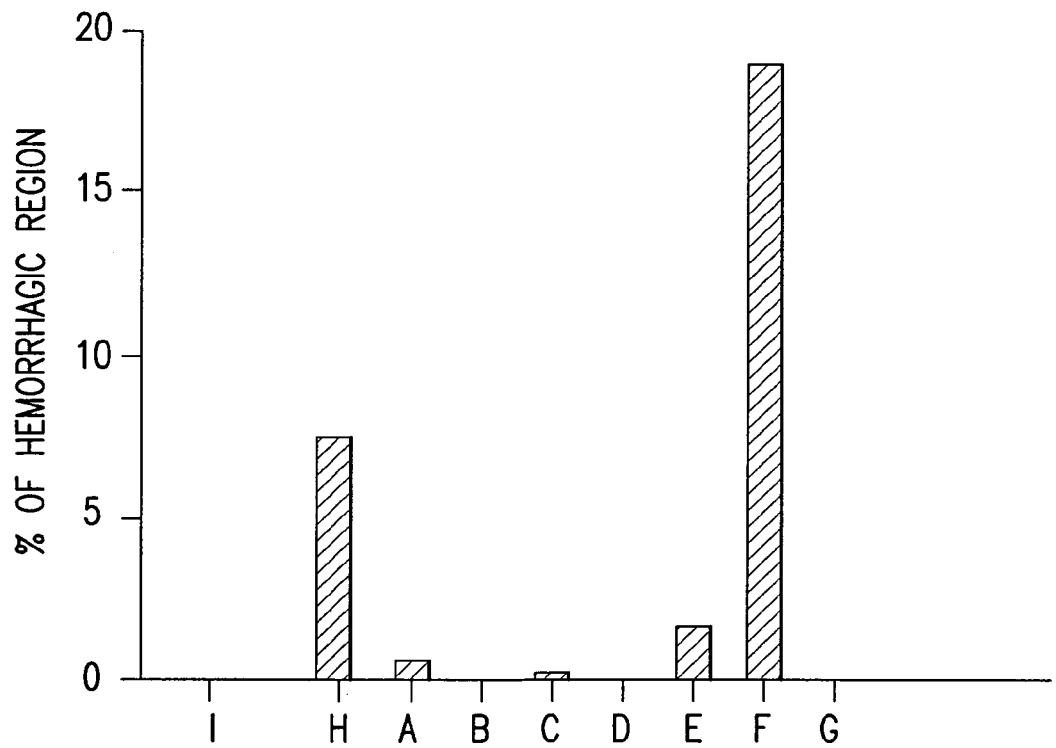
FIG. 2A shows a diagram of the relative percent area of gastric mucosal lesion as measured by a scanner and an image processing program. I is a negative standard (I=0%).
Figure 2B:
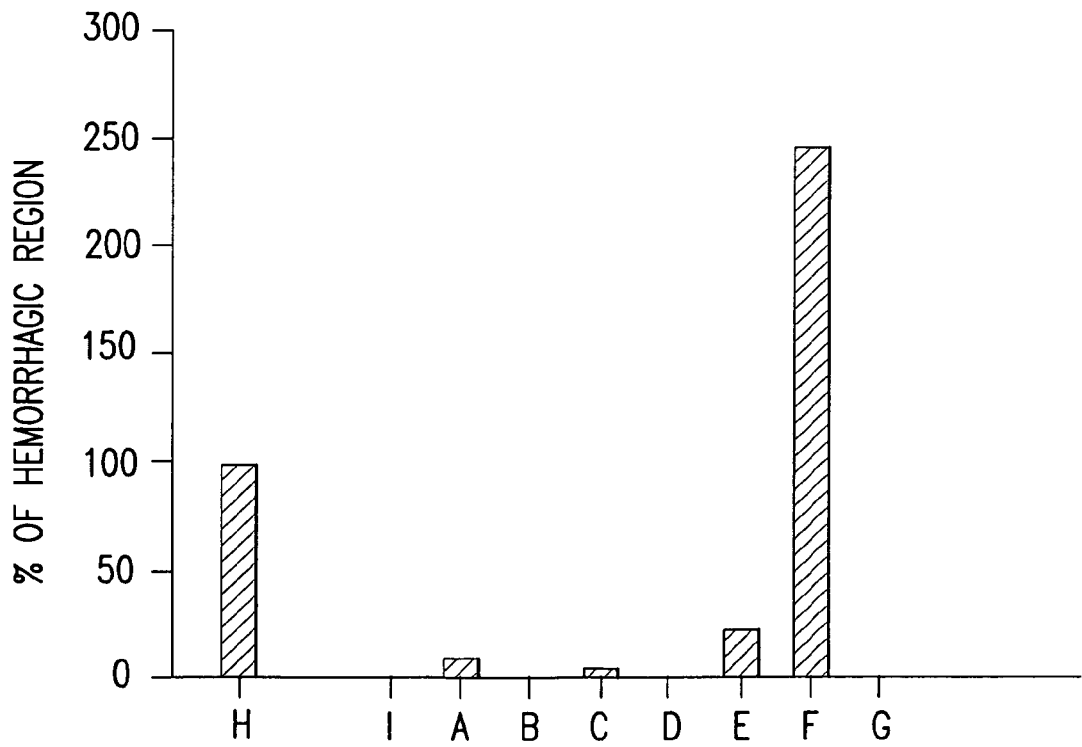
FIG. 2B shows a diagram of the relative percent area of gastric mucosal lesion as measured by a scanner and an image processing program. H is a positive standard (H=100%).
Figure 2C:
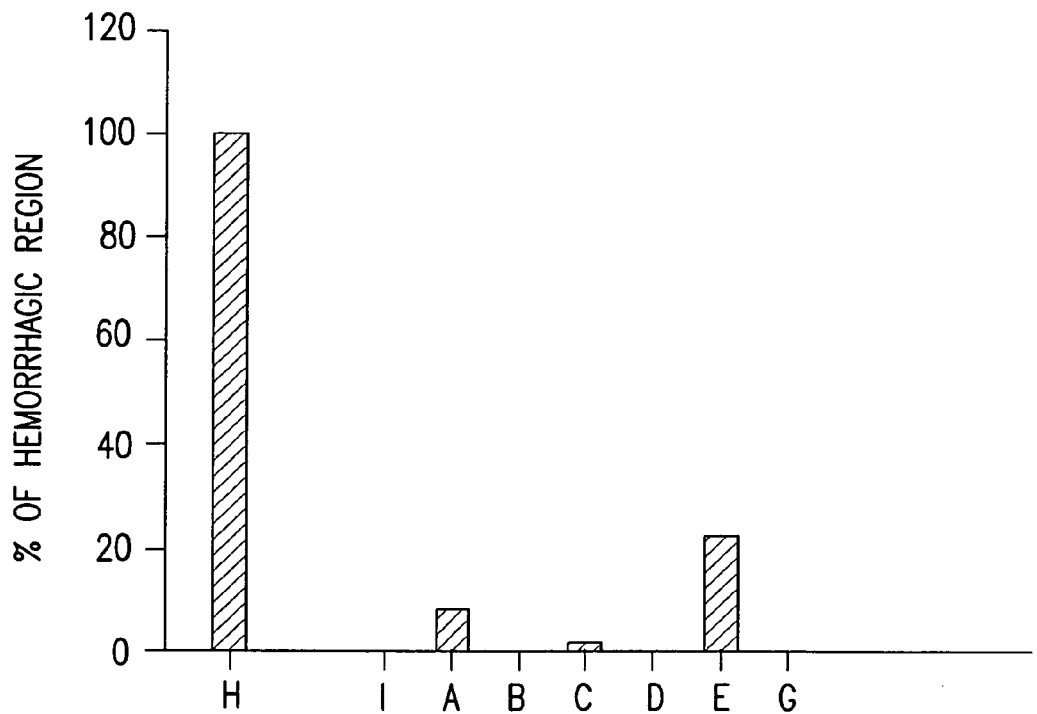
FIG. 2C shows a diagram of the relative percent area of gastric mucosal lesion as measured by a scanner and an image processing program. Peak F is excluded from the measurement since peak F is too big. H is a positive standard (H=100%).
Figure 3:
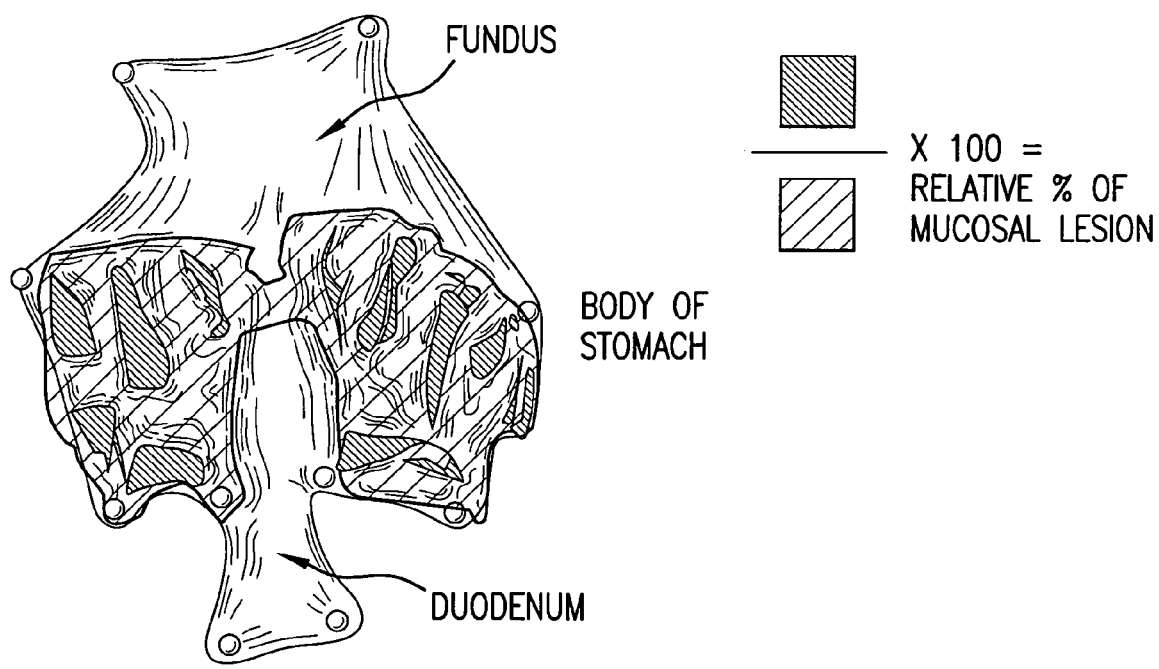
FIG. 3 shows a sketch of an example gastric mucosal lesion with markings around the mucosal lesion area and the stomach.

To allow measurement and comparison of the areas of gastric glandular mucosal lesion, the relative percentages of gastric hemorrhage were determined by image scanning and processing in accordance with Example 4. The relative percentages of gastric hemorrhage (mucosal lesion), were A, 0.68%; B, 0%; C, 0.17%; D, 0%; E, 1.76%; F, 19.02%; G, 0%; H, 7.66%; and I, 0% respectively (FIG. 2A). The relative percentages of gastric hemorrhage, where H was a standard (100%), were A, 8.88%; B, 0%; C, 2.22%; D, 0%; E, 22.98%; F, 248.30%; G, 0%; H, 100%; and I, 0% respectively (FIG. 2B). The relative percentages of gastric hemorrhage, where H was a standard (100%) and peak F was excluded, were A, 8.88%; B, 0%; C, 2.22%; D, 0%; E, 22.98%; G, 0%; H, 100%; and I, 0% respectively (FIG. 2C).

An aqueous solution of solubilized UDCA completely blocked gasrtointestinal injury such as hemorrhage, ulcer, edema and vacuole by a gastrointestinal irritant, acidic alcohol.

Example 6

Conclusions

Animal experiments on the pathogenesis of NSAIDs, alcohol, diluted alcohol and gastric irritating drug (antibiotics, adrenal corticoid steroid, anti-cancer drug)-induced gastric mucosal injury suggest that the initial event is disruption of the vascular endothelium resulting in an increased vascular permeability, followed by vascular stasis and congestion. Furthermore, nonhemorrhagic mucosa adjacent to the hemorrhagic lesions commonly exhibited striking edema, vacuolization, and necrosis of the luminal epithelial cells. For this mucosal damage there is growing evidence that oxygen-derived free radicals play a role in the pathogenesis of various disorders of the digestive system such as gastric ulcer. Recently, much attention has been focused on the role of reactive oxygen species, including superoxide, hydroxyl radicals, and hydrogen peroxide in mediating alcoholic tissue damage. Free radical scavengers have a protective effect against gastro-duodenal injury, and levels of these reactive oxygen species can be reduced by antioxidants. Furthermore, lipid peroxidation mediated by free radicals is believed to be one of the important causes of cell membrane destruction and cell damage, because the cell membrane contains many lipids, especially unsaturated fatty acids. Lipid peroxidation leads to loss of membrane fluidity and impairment of ion transport and membrane integrity on the surface of epithelial cells and helps to generate gastric lesions. It has been demonstrated that the mucosal barrier does not hinder the diffusion of ethanol into the gastric mucosa. Therefore, it might be assumed that the relatively lipophilic ethanol can also be taken up by the cells. Thus, the oxidative metabolism of ethanol may generate free radicals.

UDCA has strong antioxidant properties. The OH free radical scavenging efficiency of UDCA appears remarkable, considering that its rate constant for reaction with radical species is about 10-fold higher than that of the well known pharmacological scavenger mannitol and of the physiological scavengers glucose or histidine. Thus, given also the high therapeutic concentration of solubilized UDCA reached in gastrointestinal track, an aqueous solution of solubilized UDCA could readily act as an effective oxidant and OH free radical scavenger.

An aqueous solution of solubilized UDCA completely protects gastro intestine from injuries by the use of NSAIDs, alcohol, diluted alcohol and gastric irritating drug (antibiotics, adrenal corticoid steroid, anti-cancer drug) dose dependent manner.

What is claimed is:

1. A method of ameliorating or eliminating in a subject at least one adverse gastrointestinal effect of a composition, said method comprising:
    administering the composition to the subject; and
    administering to the subject an aqueous solution substantially free of precipitates or particles comprising:
    (a) a first material selected from the group consisting of a bile acid, a bile acid salt, and a bile acid conjugated with an amine by an amide linkage;
    (b) a carbohydrate selected from the group consisting of an aqueous soluble starch conversion product or an aqueous soluble non-starch polysaccharide; and
    (c) water, wherein the first material and the carbohydrate both remain in solution for all pH values obtainable in an aqueous system;
    wherein the composition comprises over about 20% ethanol (w/w).

2. A method according to claim 1, wherein the adverse gastrointestinal effect comprises an effect selected from the group consisting of gastroduodenal mucosal cell death, gastrointestinal necrosis, gastrointestinal apoptosis, gastroduodenal mucosal lesion, gastroduodenal mucosal erosion, gastroduodenal ulcer, gastrointestinal cancer, gastrointestinal bleeding, epigastralgia, gastritis, gastrointestinal redness, gastrointestinal edema, and combinations thereof.

3. A method according to claim 1, wherein the adverse gastrointestinal effect comprises an adverse effect on the gastro duodenum.

4. The method of claim 1, wherein the composition comprises a compound selected from the group consisting of aspirin, methyl salicylate, diflunisal, diclofenac, ibuprofen, ketoprofen, ketorolac, mefenamic acid, piroxicam, meloxicam, rofecoxib, valdecoxib, parecoxib, etoricoxib, nimesulide, mercaptopurine, methotrexate, cortisol, prednisone, methylprednisolone, fluprednisolone, bethamethasone, fludrocortisone, desoxycorticosterone acetate, and combinations thereof.

5. A method according to claim 1, wherein the subject is a mammal.

6. A method according to claim 5, wherein the subject is a human.

7. A method according to claim 1, wherein the first material is present in a therapeutically effective amount.

8. A method according to claim 1, wherein the first material is selected from the group consisting of chenodeoxycholic acid, cholic acid, hyodeoxycholic acid, deoxycholic acid, 7-oxolithocholic acid, lithocholic acid, iododeoxycholic acid, iocholic acid, tauroursodeoxycholic acid, taurochenodeoxycholic acid, taurodeoxycholic acid, glycoursodeoxycholic acid, taurocholic acid, glycocholic acid, their derivatives at a hydroxyl or carboxylic acid group on the steroid nucleus, their salts, or their conjugates with amines.

9. A method according to claim 1, wherein the aqueous soluble starch conversion product is selected from the group consisting of maltodextrin, dextrin, liquid glucose, corn syrup solid, and soluble starch.

10. A method according to claim 1, wherein the pH of the aqueous solution is between about 1 and about 10.

11. A method according to claim 1, wherein the first material is ursodeoxycholic acid or a sodium salt of ursodeoxycholic acid.

12. A method according to claim 1, wherein the aqueous soluble starch conversion product comprises maltodextrin.

13. A method according to claim 1, wherein the aqueous soluble starch conversion product comprises corn syrup solid.

14. A method according to claim 1, wherein the aqueous soluble non-starch polysaccharide is selected from the group consisting of dextran, guar gum, pectin, indigestible soluble fiber.

15. A method of ameliorating or eliminating in a subject at least one adverse gastrointestinal effect of a composition, said method comprising:
    administering the composition to the subject; and
    administering to the subject an aqueous solution substantially free of precipitates or particles comprising:
    (a) a first material selected from the group consisting of a bile acid, a bile acid salt, and a bile acid conjugated with an amine by an amide linkage;
    (b) a carbohydrate selected from the group consisting of an aqueous soluble starch conversion product or an aqueous soluble non-starch polysaccharide; and (c) water, wherein the first material and the carbohydrate both remain in solution for all pH values obtainable in an aqueous system;

wherein the composition comprises up to 100% ethanol (w/w).

16. A method according to claim 15, wherein the adverse gastrointestinal effect comprises an effect selected from the group consisting of gastroduodenal mucosal cell death, gastrointestinal necrosis, gastrointestinal apoptosis, gastroduodenal mucosal lesion, gastroduodenal mucosal erosion, gastroduodenal ulcer, gastrointestinal cancer, gastrointestinal bleeding, epigastralgia, gastritis, gastrointestinal redness, gastrointestinal edema, and combinations thereof.

17. A method according to claim 15, wherein the adverse gastrointestinal effect comprises an adverse effect on the gastro duodenum.

18. The method of claim 15, wherein the composition comprises a compound selected from the group consisting of aspirin, methyl salicylate, diflunisal, diclofenac, ibuprofen, ketoprofen, ketorolac, mefenamic acid, piroxicam, meloxicam, rofecoxib, valdecoxib, parecoxib, etoricoxib, nimesulide, mercaptopurine, methotrexate, cortisol, prednisone, methylprednisolone, fluprednisolone, bethamethasone, fludrocortisone, desoxycorticosterone acetate, and combinations thereof.

19. A method according to claim 15, wherein the subject is a mammal.

20. A method according to claim 19, wherein the subject is a human.

21. A method according to claim 15, wherein the first material is present in a therapeutically effective amount.

22. A method according to claim 15, wherein the first material is selected from the group consisting of chenodeoxycholic acid, cholic acid, hyodeoxycholic acid, deoxycholic acid, 7-oxolithocholic acid, lithocholic acid, iododeoxycholic acid, iocholic acid, tauroursodeoxycholic acid, taurochenodeoxycholic acid, taurodeoxycholic acid, glycoursodeoxycholic acid, taurocholic acid, glycocholic acid, their derivatives at a hydroxyl or carboxylic acid group on the steroid nucleus, their salts, or their conjugates with amines.

23. A method according to claim 15, wherein the aqueous soluble starch conversion product is selected from the group consisting of maltodextrin, dextrin, liquid glucose, corn syrup solid, and soluble starch.

24. A method according to claim 15, wherein the pH of the aqueous solution is between about 1 and about 10.

25. A method according to claim 15, wherein the first material is ursodeoxycholic acid or a sodium salt of ursodeoxycholic acid.

26. A method according to claim 15, wherein the aqueous soluble starch conversion product comprises maltodextrin.

27. A method according to claim 15, wherein the aqueous soluble starch conversion product comprises corn syrup solid.

28. A method according to claim 15, wherein the aqueous soluble non-starch polysaccharide is selected from the group consisting of dextran, guar gum, pectin, indigestible soluble fiber.

29. A method of ameliorating or eliminating in a subject at least one adverse gastrointestinal effect induced by a composition having mechanisms of gastrointestinal irritation identical to acidified ethanol, said method comprising:

administering the composition having a mechanism of gastrointestinal irritation identical to acidified ethanol to the subject;

administering to the subject an aqueous solution substantially free of precipitates or particles comprising:

(a) a first material selected from the group consisting of a bile acid, a bile acid salt, and a bile acid conjugated with an amine by an amide linkage;

(b) a carbohydrate selected from the group consisting of an aqueous soluble starch conversion product or an aqueous soluble non-starch polysaccharide; and (c) water, wherein the first material and the carbohydrate both remain in solution for all pH values obtainable in an aqueous system;

wherein the adverse gastrointestinal effect is selected from the group consisting of gastroduodenal mucosal cell death, gastrointestinal necrosis, gastrointestinal apoptosis, gastroduodenal mucosal lesion, gastroduodenal mucosal erosion, gastroduodenal ulcer, gastrointestinal cancer, gastrointestinal bleeding, epigastralgia, gastritis, gastrointestinal redness, gastrointestinal edema, and combinations thereof.

* * * * *